(12) United States Patent
Pacetti et al.

(10) Patent No.: US 7,361,726 B2
(45) Date of Patent: Apr. 22, 2008

(54) POLY(HYDROXYALKANOATE-CO-ESTER AMIDES) AND AGENTS FOR USE WITH MEDICAL ARTICLES

(75) Inventors: Stephen D. Pacetti, San Jose, CA (US); Syed F. A. Hossainy, Fremont, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 11/704,829

(22) Filed: Feb. 8, 2007

(65) Prior Publication Data

US 2007/0149724 A1 Jun. 28, 2007

Related U.S. Application Data

(63) Continuation of application No. 11/035,816, filed on Jan. 14, 2005, now Pat. No. 7,202,325.

(51) Int. Cl.
C08G 63/02 (2006.01)
(52) U.S. Cl. ............... 528/272; 424/78.3; 424/423; 525/54.1; 525/54.2
(58) Field of Classification Search ............ 424/78.3, 424/423; 525/54.1, 54.2; 528/271, 272
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,304,767 A | 12/1981 | Heller et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,399,665 A | 3/1995 | Barrera et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,581,387 A | 12/1996 | Cahill |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |

(Continued)

FOREIGN PATENT DOCUMENTS

DE 42 24 401 1/1994

(Continued)

OTHER PUBLICATIONS

U.S. Appl. No. 09/406,473, filed Sep. 27, 1999, Pacetti.

(Continued)

Primary Examiner—Terressa Boykin
(74) Attorney, Agent, or Firm—Squire, Sanders & Dempsey L.L.P.

(57) ABSTRACT

Polymers containing poly(hydroxyalkanoate-co-ester amides) and agents for use with medical articles are disclosed along with methods of fabricating medical articles comprising these polymers. The medical articles generally comprise an implantable substrate having a coating containing a poly(hydroxyalkanoate-co-ester amide).

20 Claims, No Drawings

U.S. PATENT DOCUMENTS

| | | |
|---|---|---|
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,001,117 A | 12/1999 | Huxel et al. |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,100,346 A | 8/2000 | Jamiolkowski et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,274,164 B1 | 8/2001 | Novich |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,548,569 B1 | 4/2003 | Williams et al. |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossainy et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |

| Patent No. | Date | Inventor |
|---|---|---|
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,703,040 B2 | 3/2004 | Katsarava |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,790,228 B2 | 9/2004 | Hossainy |
| 6,818,063 B1 | 11/2004 | Kerrigan |
| 6,824,559 B2 | 11/2004 | Michal |
| 6,926,919 B1 | 8/2005 | Hossainy et al. |
| 7,005,137 B1 | 2/2006 | Hossainy et al. |
| 7,022,334 B1 | 4/2006 | Ding |
| 7,056,591 B1 | 6/2006 | Pacetti et al. |
| 7,074,276 B1 | 7/2006 | Sciver et al. |
| 7,135,038 B1 | 11/2006 | Limon |
| 7,169,178 B1 | 1/2007 | Santos et al. |
| 7,175,874 B1 | 2/2007 | Pacetti |
| 7,201,935 B1 | 4/2007 | Claude et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0156150 A1* | 10/2002 | Williams et al. ............ 523/113 |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0104028 A1 | 6/2003 | Hossainy et al. |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0208259 A1 | 11/2003 | Penhasi |
| 2003/0211230 A1 | 11/2003 | Pacetti et al. |
| 2003/0236320 A1 | 12/2003 | Martin et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0098118 A1 | 5/2004 | Granada et al. |
| 2004/0180132 A1 | 9/2004 | Pacetti |
| 2004/0191405 A1 | 9/2004 | Kerrigan |
| 2004/0253203 A1 | 12/2004 | Hossainy |
| 2005/0021127 A1 | 1/2005 | Kawula |
| 2005/0025799 A1 | 2/2005 | Hossainy |
| 2005/0074544 A1 | 4/2005 | Pacetti et al. |
| 2005/0208093 A1 | 9/2005 | Glauser et al. |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |

| | | |
|---|---|---|
| JP | 06001841 | 1/1994 |
| JP | 11035680 | 2/1999 |
| JP | 11302374 | 11/1999 |
| JP | 2001048794 | 2/2001 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | 0 301 856 | 2/1989 |
| SU | 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36013 | 8/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/24247 | 3/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO04/000383 | 12/2003 |
| WO | WO2004/009145 | 1/2004 |
| WO | WO2005/000939 | 1/2005 |

OTHER PUBLICATIONS

U.S. Appl. No. 09/748,412, filed Dec. 21, 2000, Roorda.
U.S. Appl. No. 09/966,786, filed Sep. 27, 2001, Hossainy.
U.S. Appl. No. 09/967,632, filed Sep. 28, 2001, Pacetti.
U.S. Appl. No. 10/040,538, filed Dec. 28, 2001, Pacetti et al.
U.S. Appl. No. 10/099,101, filed Mar. 15, 2002, Hossainy.
U.S. Appl. No. 10/104,772, filed Mar. 20, 2002, Dutta.
U.S. Appl. No. 10/108,004, filed Mar. 27, 2002, Hossainy et al.
U.S. Appl. No. 10/177,154, filed Jun. 21, 2002, Hossainy et al.
U.S. Appl. No. 10/176,504, filed Jun. 21, 2002, Roorda et al.
U.S. Appl. No. 10/177,117, filed Jun. 21, 2002, Hossainy.
U.S. Appl. No. 10/177,942, filed Jun. 21, 2002, Michal et al.
U.S. Appl. No. 10/199,272, filed Jul. 18, 2002, Ding.
U.S. Appl. No. 10/246,883, filed Sep. 18, 2002, Taylor.
U.S. Appl. No. 10/255,911, filed Sep. 26, 2002, Ding.
U.S. Appl. No. 10/260,182, filed Sep. 27, 2002, Hossainy.
U.S. Appl. No. 10/266,479, filed Oct. 8, 2002, Hossainy.
U.S. Appl. No. 10/271,851, filed Oct. 15, 2002, Roorda.
U.S. Appl. No. 10/286,058, filed Oct. 31, 2002, Pacetti et al.
U.S. Appl. No. 10/316,739, filed Dec. 10, 2002, Zhang et al.
U.S. Appl. No. 10/327,371, filed Dec. 19, 2002, Lin et al.
U.S. Appl. No. 10/330,412, filed Dec. 27, 2002, Hossainy et al.
U.S. Appl. No. 10/375,497, filed Feb. 26, 2003, Pacetti.
U.S. Appl. No. 10/376,348, filed Feb. 26, 2003, Ding et al.
U.S. Appl. No. 10/375,496, filed Feb. 26, 2003, Esbeck.
U.S. Appl. No. 10/376,027, filed Feb. 26, 2003, Kokish et al.
U.S. Appl. No. 10/382,197, filed Mar. 4, 2003, Pacetti.
U.S. Appl. No. 10/428,691, filed May 1, 2003, Pacetti.
U.S. Appl. No. 10/438,378, filed May 15, 2003, Esbeck et al.
U.S. Appl. No. 10/606,711, filed Jun. 26, 2003, Pacetti.
U.S. Appl. No. 10/606,712, filed Jun. 26, 2003, Pacetti.
U.S. Appl. No. 10/631,116, filed Jul. 31, 2003, Dehnad.
U.S. Appl. No. 10/703,334, filed Nov. 6, 2003, Pacetti.
U.S. Appl. No. 10/705,546, filed Nov. 10, 2003, Kwok et al.
U.S. Appl. No. 10/714,111, filed Nov. 14, 2003, Claude.
U.S. Appl. No. 10/718,278, Nov. 19, 2003, Hossainy et al.
U.S. Appl. No. 10/718,976, filed Nov. 20, 2003, Hossainy et al.
U.S. Appl. No. 10/719,516, filed Nov. 21, 2003, Tang et al.
U.S. Appl. No. 10/725,698, filed Dec. 1, 2003, Pacetti.
U.S. Appl. No. 10/729,728, filed Dec. 5, 2003, Pacetti.
U.S. Appl. No. 10/729,551, filed Dec. 5, 2003, Pacetti.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/746,483, filed Dec. 24, 2003, Galuser et al.
U.S. Appl. No. 10/750,139, filed Dec. 30, 2003, Desnoyer et al.
U.S. Appl. No. 10/751,043, filed Jan. 2, 2004, Hossainy et al.
U.S. Appl. No. 10/751,289, filed Jan. 2, 2004, Hossainy et al.
U.S. Appl. No. 10/722,858, filed Feb. 4, 2004, Hossainy et al.
U.S. Appl. No. 10/805,036, filed Mar. 16, 2004, Pacetti.
U.S. Appl. No. 10/812,780, filed Mar. 29, 2004, Tang et al.
U.S. Appl. No. 10/813,845, filed Mar. 30, 2004, Pacetti et al.
U.S. Appl. No. 10/815,421, filed Mar. 31, 2004, Hossainy.
U.S. Appl. No. 10/816,072, filed Mar. 31, 2004, Dugan et al.
U.S. Appl. No. 10/817,642, filed Apr. 2, 2004, Kerrigan.
U.S. Appl. No. 10/835,229, filed Apr. 28, 2004, Prabhu et al.
U.S. Appl. No. 10/835,656, filed Apr. 30, 2004, Tang et al.
U.S. Appl. No. 10/835,912, filed Apr. 30, 2004, Hossainy et al.
U.S. Appl. No. 10/851,411, filed May 20, 2004, Chen.
U.S. Appl. No. 10/853,924, filed May 25, 2004, Pathak.
U.S. Appl. No. 10/855,025, filed May 26, 2004, Dang.
U.S. Appl. No. 10/855,294, filed May 26, 2004, Pacetti et al.
U.S. Appl. No. 10/877,419, filed Jun. 25, 2004, Pacetti.
U.S. Appl. No. 10/881,540, filed Jun. 29, 2004, Hossainy et al.
U.S. Appl. No. 10/883,242, filed Jun. 30, 2004, Roorda et al.
U.S. Appl. No. 10/882,506, filed Jun. 30, 2004, Stewart et al.
U.S. Appl. No. 10/909,795, filed Jul. 30, 2004, Ding et al.
U.S. Appl. No. 10/902,982, filed Jul. 30, 2004, Pacetti et al.
U.S. Appl. No. 10/910,453, filed Aug. 2, 2004, Hossainy et al.
U.S. Appl. No. 10/913,607, filed Aug. 5, 2004, Pacetti et al.
U.S. Appl. No. 10/820,316, filed Aug. 7, 2004, Hossainy et al.
U.S. Appl. No. 10/928,587, filed Aug. 26, 2004, Hossainy et al.
U.S. Appl. No. 10/932,364, filed Aug. 31, 2004, Foreman et al.
U.S. Appl. No. 10/931,927, filed Aug. 31, 2004, Pacetti.
U.S. Appl. No. 10/948,036, filed Sep. 22, 2004, Pacetti et al.
U.S. Appl. No. 10/960,381, filed Oct. 6, 2004, Desnoyer.
U.S. Appl. No. 10/975,247, filed Oct. 27, 2004, Desnoyer et al.
U.S. Appl. No. 10/976,550, filed Oct. 29, 2004, Pacetti et al.
U.S. Appl. No. 10/976,551, filed Oct. 29, 2004, Desnoyer et al.
U.S. Appl. No. 10/978,031, filed Oct. 29, 2004, Pacetti.
U.S. Appl. No. 10/976,550, filed Oct. 29, 2004, Pacetti et al.
U.S. Appl. No. 10/978,031, filed Oct. 29, 2004, Pacetti.
U.S. Appl. No. 10/999,391, filed Nov. 29, 2004, Hossainy.
U.S. Appl. No. 11/000,572, filed Nov. 30, 2004, Pacetti.
U.S. Appl. NO. 11/015,313, filed Dec. 16, 2004, Pacetti et al.
U.S. Appl. No. 11/015,943, filed Dec. 17, 2004, Roorda et al.
U.S. Appl. No. 11/021,775, filed Dec. 22, 2004, Pacetti.

U.S. Appl. No. 11/023,837, filed Dec. 27, 2004, Hossainy.
U.S. Appl. No. 11/027,822, filed Dec. 29, 2004, Ding.
U.S. Appl. No. 11/027,955, filed Dec. 30, 2004, Hossainy et al.
Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
International Search Report for PCT/US2005/043514, filed Dec. 2, 2005, mailed May 4, 2006, 6 pgs.
Aoyagi et al., *Preparation of cross-linked aliphatic polyester and application to thermo-responsive material*, Journal of Controlled Release 32:87-96 (1994).
Arvanitoyannis, I., et al., "Synthesis and study of novel biodegradable oligo(ester amide)s based on sebacic acid, octadecanedioic acid, 1,6-hexanediamine and ε-caprolactone: 2," Polymer, Elsevier Science Publishers B.V., GB, vol. 36, No. 4, pp. 857-866, Feb. 1995.
Barath et al., *Low Dose of Antitumor Agents Prevents Smooth Muscle Cell Proliferation After Endothelial Injury*, JACC 13(2): 252A (Abstract) (Feb. 1989).
Barrera, D.A., et al., Copolymerization and Degradation of Poly(lactic acid-co-lysine), Macromolecules, ACS, Washington, DC, US, vol. 28, No. 2, pp. 425-432, Jan. 16, 1995.
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
D'Angelo, S., et al., "Segmented poly(ether-ester-amide)s based on poly(L,L-lactide) macromers," Polymer, Elsevier Science Publishers B.V., GB, vol. 42, No. 8, pp. 3383-3392, Apr. 2001.
De Lezo et al., *Intracoronary Ultrasound Assessment of Directional Coronary Atherectomy: Immediate and Follow-Up Findings*, JACC vol. 21, No. 2, (1993) pp. 298-307.
De Simone, V., et al., "Synthesis, Characterization, and Degradation of Block Polyesteramides Containing Poly(l-Lactide) Segments," Journal of Applied Polymer Science, John Wiley and Sons Inc., NY, US, vol. 46, No. 10, pp. 1813-1820, Dec. 5, 1992.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(esteramide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials For Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Moreno et al., *Macrophage Infiltration Predicts Restenosis After Coronary Intervention in Patients with Unstable Angina*, Circulation, vol. 94, No. 12, (1996) pp. 3098-3102.
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Oikawa et al., *Mechanisms of Acute Gain and Late Lumen Loss After Atherectomy in Different Preintervention Arterial Remodeling Patterns*, The Am. J. of Cardiology, vol. 89, (2002) pp. 505-510.
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Scully et al., *Effect of a heparan sulphate with high affinity for antithrombin III upon inactivation of thrombin and coagulaton Factor Xa*, Biochem J. 262, (1989) pp. 651-658.
Shigeno, *Prevention of Cerebrovascular Spasm By Bosentan, Novel Endothelin Receptor*, Chemical Abstract 125:212307 (1996).
van Beusekom et al., *Coronary stent coatings*, Coronary Artery Disease 5(7):590-596 (Jul. 1994).
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
Wang, D., et al., "Copolymerization of $_\epsilon$-Caprolactone with (3S)-3-[(Benzyloxycarbonyl)methyl]morpholine-2,5-dione and the $^{13}$C NMR Sequence Analysis of the Copolymer," Macromolecules, ACS, Washington, DC, US, vol. 31, No. 12, pp. 3824-3831, Jun. 16, 1998.
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

POLY(HYDROXYALKANOATE-CO-ESTER AMIDES) AND AGENTS FOR USE WITH MEDICAL ARTICLES

CROSS-REFERENCE TO RELATED APPLICATION

This application is a continuation application of U.S. application Ser. No. 11/035,816, filed on Jan. 14, 2005 now U.S. Pat. No. 7,202,325.

BACKGROUND

1. Field of the Invention

This invention is directed to polymers for use with medical articles and, more specifically, copolymers of poly(hydroxyalkanoate-co-ester amides).

2. Description of the State of the Art

A current paradigm in biomaterials research is the control of protein adsorption on an implant surface. Uncontrolled protein adsorption on an implant surface is a problem with current biomaterial implants and leads to a mixed layer of partially denatured proteins on the implant surface. This mixed layer of partially denatured proteins leads to disease, for example, by providing cell-binding sites from adsorbed plasma proteins such as fibrinogen and immunoglobulin G. Platelets and inflammatory cells such as, for example, monocytes, macrophages and neutrophils, adhere to the cell-binding sites. A wide variety of proinflammatory and proliferative factors may be secreted and result in a diseased state. Accordingly, a non-fouling surface, which is a surface which does not become fouled or becomes less fouled with this layer of partially denatured proteins, is desirable.

A stent is an example of an implant that can benefit from a non-fouling surface. Stents are a mechanical intervention that can be used as a vehicle for delivering pharmaceutically active agents. As a mechanical intervention, stents can physically hold open and, if desired, expand a passageway within a subject. Typically, a stent may be compressed, inserted into a small vessel through a catheter, and then expanded to a larger diameter once placed in a proper location. Examples of patents disclosing stents include U.S. Pat. Nos. 4,733,665, 4,800,882 and 4,886,062.

Stents play an important role in a variety of medical procedures such as, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted to reduce occlusions, inhibit thrombosis and restenosis, and maintain patency within vascular lumens such as, for example, the lumen of a coronary artery.

Local delivery of agents is often preferred over systemic delivery of agents, particularly where high systemic doses are necessary to achieve an effect at a particular site within a subject, because high systemic doses of agents can often create adverse effects within the subject. One proposed method of local delivery includes coating the surface of a medical article with a polymeric carrier and attaching an agent to, or blending the agent with, the polymeric carrier.

Some of the currently desired polymeric materials such as, for example, the poly(hydroxyalkanoates) are biodegradable. Unfortunately, these polymers do not have sufficient mechanical properties for a number of medical applications. For example, the mechanical properties of currently available poly(hydroxyalkanoates) have been found to be insufficient for many stent applications. Accordingly, there is a need for poly(hydroxyalkanoates) with improved mechanical properties.

Another set of problems are associated with the release of agents from biodegradable coatings within a subject. One problem is that the release rate and absorption rate of biodegradable coatings should be controllable. The absorption rate of currently available poly(hydroxyalkanoates), for example, is too slow for most applications. Another problem involves regulatory concerns in that molecules from a polymeric carrier may remain attached to an agent upon breakdown of the coating. Since these additional molecules were not considered in the original regulatory approval of the agent, there may be regulatory concerns over possible changes in the agent's biological activity.

Accordingly, there is a need for poly(hydroxyalkanoate) coatings (i) that have sufficient mechanical properties for applications that can benefit from biodegradable polymers, (ii) that can release agents that are substantially free of additional molecules derived from a polymeric carrier, (iii) that can be designed to have a predetermined release rate and absorption rate; and (iv) that can be combined with agents that are not only bioactive and/or biobeneficial but also control a physical property and/or a mechanical property of a medical article formed from the polymer.

SUMMARY

Embodiments of the present invention generally encompass polymers containing poly(hydroxyalkanoates) and agents such as diagnostic, prophylactic, therapeutic, ameliorative, and other agents, for use with medical articles. The polymers can be used in medical articles such as, for example, stents, as well as coatings for such medical articles.

In some embodiments, the invention can include a polymer ("the poly(HA-EA) copolymer") represented by the following formula:

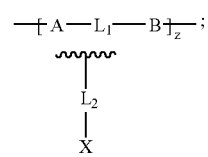

wherein A comprises

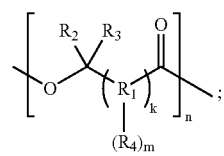

and, the ratio of A:B is less than, greater than, or equal to one. Each $R_1$ comprises a component that is independently selected from a group consisting of alkylenes, alkanoates, alkyl alkanoates, diesters, acylals, diacids, saturated fatty acids, glycerides, and combinations thereof. Each of $R_2$ through $R_4$ comprises a component that is independently selected from a group consisting of hydrogen; substituted, unsubstituted, hetero-, straight-chained, branched, cyclic, saturated and unsaturated aliphatic radicals; and substituted, unsubstituted, and hetero-aromatic radicals. At least one of $L_1$, B, $L_2$ or X is optional; and, at least one of $L_1$, B, $L_2$ or X comprises an ester amide, wherein $L_1$ is a linkage connecting A to B, X is an optional moiety, $L_2$ is a linkage connecting X to the polymer, k and m are integers, and n and z are integers not equal to zero.

In other embodiments, the invention can include a method comprising fabricating (i) a medical article comprising an implantable substrate or (ii) a coating for the medical article, wherein said fabricating comprises preparing ("the poly (HA-EA) copolymer"); forming a medical article or coating comprising the polymer on at least a portion of an implantable substrate; and optionally annealing the medical article or coating. In other embodiments, the invention can include a drug-eluting stent comprising a poly(hydroxyalkanoate-co-ester amide).

DETAILED DESCRIPTION

As discussed in more detail below, embodiments of the present invention generally encompass compositions including poly(hydroxyalkanoate-co-ester amides) ("p(HA-EA)") and an agent such as, for example, a therapeutic, prophylactic, diagnostic and/or other agent, for use with medical articles. The invention also encompasses methods for fabricating the compositions. The medical articles comprise any medical device such as, for example, an implantable medical device such as a stent. In some embodiments, the compositions can be used as a coating on the implantable substrate. In other embodiments, a medical device such as a stent is made in whole or in part from the composition.

An "agent" can be a moiety that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical articles that can be improved through the teachings described herein are within the scope of the present invention. Examples of medical devices include, but are not limited to, stents, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts (AXIUS™, Guidant Corp.) and endocardial leads (FINELINE® and ENDOTAK®, Guidant Corp.).

The medical devices can be comprised of a metal or an alloy, including, but not limited to, ELASTINITE® (Guidant Corp.), NITINOL® (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc.; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that are comprised of bioabsorbable polymers or biostable polymers are also included within the scope of the present invention.

The Polymeric Compositions

The p(HA-EA) compositions of the present invention include any combination of polymers, copolymers and agents, wherein the combination comprises a hydroxyalkanoate moiety and an ester amide moiety. These polymers can be biodegradable due to the labile nature of the ester groups that are present. Accordingly, these compositions can be designed such that they can be broken down, absorbed, resorbed and eliminated by a mammal. The compositions of the present invention can be used, for example, to form medical articles and coatings.

The terms "combine," "combined," and "combining" all refer to a relationship between components of a composition and include blends, mixtures, linkages, and combinations thereof, of components that form the compositions. The linkages can be connections that are physical, chemical, or a combination thereof. Examples of physical connections include, but are not limited to, an interlinking of components that can occur, for example, in interpenetrating networks and chain entanglement. Examples of chemical connections include, but are not limited to, covalent and non-covalent bonds. Covalent bonds include, but are not limited to, simple covalent bonds and coordinate bonds. Non-covalent bonds include, but are not limited to, ionic bonds, and intermolecular attractions such as, for example, hydrogen bonds and attractions created by induced and permanent dipole-dipole interactions.

Compositions that are selected for an in vivo use should meet particular requirements with regard to physical, mechanical, chemical, and biological properties of the compositions. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing. An example of a chemical property that can affect performance of a biodegradable composition in vivo is the rate of absorption of the composition by a subject. An example of a biological property that can affect performance of a composition in vivo is the bioactive and/or biobeneficial nature of the composition, both of which are described below.

While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo. In some embodiments, an increase in hydrolysis can also increase the release rate of an agent by creating channels within a medical article or coating that can serve as transport pathways for diffusion of the agents from the composition. The terms "subject" and "patient" can be used interchangeably and refer to an animal such as a mammal including, but not limited to, non-primates such as, for example, a cow, pig, horse, cat, dog, rat, and mouse; and primates such as, for example, a monkey, or a human.

The compositions of the present invention can be used to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and absorption rate; and (iv) that can be combined with agents that are not only bioactive and/or biobeneficial but also control a physical property and/or a mechanical property of a medical article or coating formed from the polymer.

For the purposes of the present invention, a polymer or coating is "biodegradable" when it is capable of being completely or substantially degraded or eroded when exposed to an in vivo environment or a representative in vitro environment. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application. The polymers used in the present invention may be biodegradable and may include, but are not limited to, condensation copolymers.

A p(HA-EA) composition of the present invention comprises at least one hydroxyalkanoate monomer and one ester amide monomer. The p(HA-EA)s can also contain a wide variety of other moieties and, as a result, can have a wide variety of molecular configurations. The chemical structure of the p(HA-EA) compositions is discussed below.

Poly(hydroxyalkanoates) can be obtained from a biological source or from a chemical synthesis. The biological source can be a microorganism, a higher organism such as a plant or a genetically modified bioreactor such as a host cell that can be a prokaryote or a eukaryote. Methods used to produce PHAs biologically are known in the art such as, for example, those methods discussed in U.S. Pat. Nos. 4,910,145; 5,245,023; 5,250,430; 5,480,794; 5,512,669; and 5,534,432. Methods of producing PHAs through chemical synthesis include, but are not limited to, ring-opening polymerization of β-lactone monomers and condensation polymerization of esters of 3-hydroxy alkanioc acids, each of which are discussed in U.S. Pat. Nos. 6,610,764 and 5,563,239, respectively.

In some embodiments, the p(HA-EA) compositions can comprise other polymers that can be combined with the p(HA-EA) to form a p(HA-EA) composition. In some embodiments, polymers other than p(HA-EA) can be crosslinked with the p(HA-EA) using, for example, an isocyanate, a diisocyanate, diacyl halide, diene, or another crosslinking agent discussed herein or known to one of skill in the art.

The amount of the polymers other than p(HA-EA) that are combined with a p(HA-EA) should be limited by the effect that the other polymers have on a desired performance parameter of a product formed from the composition. Such performance parameters may include, for example, the toughness of a medical device or coating, the capacity for the loading concentration of an agent, and the rate of biodegradation and elimination of the composition from a subject. If the other polymers in a composition are non-biodegradable, they should be sized to produce polymer fragments that can clear from the subject following biodegradation of the composition.

In some embodiments, the number average molecular weight of the polymer fragments should be at or below about 40,000 Daltons, or any range therein. In other embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

Examples of other polymers that can be combined with the p(HA-EA)s of the present invention include, but are not limited to, poly(acrylates) such as poly(butyl methacrylate), poly(ethyl methacrylate), poly(hydroxyl ethyl methacrylate), poly(ethyl methacrylate-co-butyl methacrylate), copolymers of ethylene-methyl methacrylate; poly (2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly (vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly (caprolactones); poly(lactide-co-glycolide); poly (hydroxybutyrates); poly(hydroxybutyrate-co-valerate); poly(dioxanones); poly(orthoesters); poly(anhydrides); poly (glycolic acid); poly(glycolide); poly(D,L-lactic acid); poly (D,L-lactide); poly(glycolic acid-co-trimethylene carbonate); poly(phosphoesters); poly(phosphoester urethane); poly(trimethylene carbonate); poly(iminocarbonate); poly (ethylene); poly(propylene) co-poly(ether-esters) such as, for example, poly(dioxanone) and poly(ethylene oxide)/poly (lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly (vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; poly(amides) such as Nylon 66 and poly(caprolactam); alkyd resins; poly(carbonates); poly (oxymethylenes); poly(imides); poly(ester amides); poly (ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, the other polymers are selected such that they specifically exclude any one or any combination of these polymers.

In some embodiments, the other polymers can be biodegradable. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In other embodiments, the biodegradable polymers include, but are not limited to, polyesters, poly (ester amides); amino acids; PEG and/or alcohol groups, polycaprolactones, poly(L-lactide), poly(D,L-lactide), poly (D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly (amino acids), polycyanoacrylates, poly(trimethylene carbonate), poly(imino carbonate), polycarbonates, polyurethanes, copoly(ether-esters) (e.g. PEO/PLA), poly-alkylene oxalates, polyphosphazenes, PHA-PEG, and any derivatives, analogs, homologues, salts, copolymers and combinations thereof. In other embodiments, the other polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the other polymers are selected such that they specifically exclude any one or any combination of these polymers.

In some embodiments, the other polymers can be chemically connected to a p(HA-EA) by covalent bonds. In other embodiments, the other polymers can be chemically connected to a p(HA-EA) by non-covalent bonds such as, for example, by ionic bonds, inter-molecular attractions, or a combination thereof. In other embodiments, the other polymers can be physically connected to a p(HA-EA). In other embodiments, the other polymers can be chemically and physically connected with a p(HA-EA). Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed with the p(HA-EA)s.

With respect to the chemical notation used herein, each of the functional groups R may or may not be numbered for clarity in a particular teaching and can be independently selected from any group, subgroup, or combination thereof, as specified herein. These groups, subgroups, and combinations thereof, can include H; substituted, unsubstituted, hetero-, straight-chained, branched, cyclic, saturated or unsaturated aliphatic radicals; substituted, unsubstituted, or hetero-aromatic radicals; or a combination thereof. For example, an R group can be a H; an aliphatic hydrocarbon group such as, for example, an alkyl, alkenyl, or alkynyl group; an aromatic group such as, for example, an aryl, aralkyl, aralkenyl, of aralkynyl group; various other groups as defined herein, or a combination thereof.

In some embodiments of the present invention, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 4 to about 200 carbon atoms, from about 6 to about 150 carbon atoms, from about 12 to about 120 carbon atoms, from about 18 to about 90 carbon atoms, from about 24 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, iso-octyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain including at least one alkene functionality. The term "alkynyl" refers to a straight-chained or branched carbon-containing chain including at least one alkyne functionality. The term "aryl" refers to a carbon-containing ring bearing a system of conjugated double bonds often comprising at least six $\pi$ (pi) electrons. Examples of aryl groups include, but are not limited to, phenyl, naphthyl, anysyl, toluyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of sidechains having 1 or more carbon atoms. In some embodiments, a radical is straight-chained if it has less than 0.01 mole percent of such sidechains. In other embodiments, a radical is straight-chained if it has less than 0.001 mole percent of such sidechains. A radical is "branched" when it has more than 0.1 mole percent of sidechains having 1 or more carbon atoms. In some embodiments, a radical is branched when it has more than 0.01 mole percent of such sidechains. In other embodiments, a radical is branched when it has more than 0.001 mole percent of such sidechains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted. Examples of substituents in substituted radicals include, but are not limited to, hydroxyls, alkyls, carboxyls, esters, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

In some embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In other embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In other embodiments, the functional groups can be oxygen-containing groups including, but not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In other embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In other embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In other embodiments, the functional groups can include, but are not limited to, sulfur-containing groups such as sulfones, sulfides, sulfinamides, sulfilimines, sulfimides, sulfinamides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides, sulphur diimides, thio, thioacetals, thioaldehydes, thioanhydrides, thiocarboxylic acids, thiocyanates, thioether, thiohemiacetals, thioketones, thiol, thiolates, xanthic acids, and combinations thereof.

In other embodiments, the functional groups can include, but are not limited to, silyl groups, halogens, selenoethers, trifluoromethyls, thio-derivatives of urethanes where at least one oxygen atom is replaced by a sulfur atom, phosphoryls, phosphonates, phosphinates, and combinations thereof. In other embodiments, the functional groups are capable of free-radical polymerization and can include, but are not limited to, ethylenically unsaturated groups such as, for example, allyl, vinyl, acryloyl and methacrylol, and maleate and maleimido; and combinations thereof. In other embodiments, the functional groups include halides. In other embodiments, the functional group may include light scattering groups, magnetic groups, nanogold, other proteins, a solid matrix, radiolabels, carbohydrates, and combinations thereof.

The Agents

Biobeneficial and Bioactive Agents

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to, many of the polymers listed above such as, for example, carboxymethylcellulose; poly(alkylene glycols) such as, for example, PEG; poly(N-vinyl pyrrolidone); poly (acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD). In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof, quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is m-PEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the present invention include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, and dactinomycin (COSMEGEN®, Merck & Co., Inc.). Antineoplastics or antimitotics include, for example, paclitaxel (TAXOL®, Bristol-Myers Squibb Co.), docetaxel (TAXOTERE®, Aventis S.A.), methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; methyl rapamycin; 42-Epi-(tetrazoylyl)rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

Examples of diagnostic agents include radioopaque materials and include, but are not limited to, materials comprising iodine or iodine-derivatives such as, for example, iohexal and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomagraphy (PET). Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

Plasticizing Agents

The terms "plasticizer" and "plasticizing agent" can be used interchangeably in the present invention, and refer to any agent, including any agent described above, where the agent can be added to a polymeric composition to modify the mechanical properties of the composition or a product formed from the composition. Plasticizers can be added, for example, to reduce crystallinity, lower the glass-transition temperature ($T_g$), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxy-ethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methyl pyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight.

The amount of plasticizer used in the present invention, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents.

It should be appreciated that any one or any combination of the plasticizers described above can be used in the present invention. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

It should also be appreciated that the plasticizers can be combined with other active agents to obtain other desired functions such as, for example, an added therapeutic, prophylactic, and/or diagnostic function. In some embodiments, the plasticizers can be linked to other agents through ether, amide, ester, orthoester, anhydride, ketal, acetal, carbonate, and all-aromatic carbonate linkages, which are discussed in more detail below.

In some embodiments, the agents can be chemically connected to a polymer by covalent bonds. In other embodiments, the agents can be chemically connected to a polymer by non-covalent bonds such as, for example, by ionic bonds, inter-molecular attractions, or a combination thereof. In other embodiments, the agents can be physically connected to a polymer. In other embodiments, the agents can be chemically and physically connected with a polymer.

Examples of ionic bonding can include, but are not limited to, ionic bonding of an anionic agent to a cationic site on a polymer or a cationic agent to an anionic site on a polymer. In some embodiments, an anionic agent can be bound to a quaternary amine on a polymer. In other embodiments, an agent with a quaternary amine can be bound to an anionic site on a polymer. Examples of inter-molecular attractions include, but are not limited to, hydrogen bonding such as, for example, the permanent dipole interactions between hydroxyl, amino, carboxyl, and sulfhydryl groups, and combinations thereof. Examples of physical connections can include, but are not limited to, interpenetrating networks and chain entanglement. The agents can also be blended or mixed with the PHA compositions.

In some embodiments, the agents have a reactive group that can be used to link the agents to the polymer. Examples of reactive groups include, but are not limited to, hydroxyl, acyl, amino, amido, and sulfhydryl groups. In some embodiments, the agents can be released or can separate from the polymer composition. In other embodiments, the agents can be biobeneficial, bioactive, diagnostic, plasticizing, or have a combination of these characteristics.

In some embodiments, the molecular weight of an agent should be at or below about 40,000 Daltons, or any range therein, to ensure elimination of the agent from a mammal. In one embodiment, the molecular weight of the agent ranges from about 300 Daltons to about 40,000 Daltons, from about 8,000 Daltons to about 30,000 Daltons, from about 10,000 Daltons to about 20,000 Daltons, or any range therein. If upon release, the biobeneficial agent is rapidly broken down in the body, then the molecular weight of the agent could be greater than about 40,000 Daltons without compromising patient safety. The molecular weights as taught herein are a number average molecular weight.

It should also be appreciated that the agents of the present invention can have properties that are biobeneficial, bioactive, diagnostic, plasticizing or a combination thereof. For example, classification of an agent as a biobeneficial agent does not preclude the use of that agent as a bioactive agent, diagnostic agent and/or plasticizing agent. Likewise, classification of an agent as a bioactive agent does not preclude the use of that agent as a diagnostic agent, biobeneficial agent and/or plasticizing agent. Furthermore, classification of an agent as a plasticizing agent does not preclude the use of that agent as a biobeneficial agent, bioactive agent, and/or diagnostic agent. It should also be appreciated that any of the foregoing agents can be combined with the p(HA-EA) compositions such as, for example, in the form of a medical device or a coating for a medical device. By way of a non-limiting example, a stent coated with the p(HA-EA) compositions of the invention can contain paclitaxel, docetaxel, rapamycin, methyl rapamycin, 42-Epi-(tetrazoylyl) rapamycin, or everolimus.

Concentrations of Agents

The agents of the present invention can be combined with other agents to obtain other desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by those of skill in the art when administering an agent to a subject.

It is to be appreciated that the design of a composition for the sustained release of agents can be dependent on a variety of factors such as, for example, the therapeutic, prophylactic, ameliorative or diagnostic needs of a patient. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In other embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and any range therein, where the percentage is based on the total weight of the polymer and agent or combination of agents.

The Structures of p(HA-EA)s, Copolymers and Agents

The term "p(HA-EA)" refers to a polymeric composition that contains a hydroxyalkanoate, which is a hydroxyacid moiety that contains an alkane with hydroxyl and carboxyl functionality; and an ester amide. Many known PHA compositions are brittle by themselves and, as taught herein, their physical and mechanical properties are modified by combining ester amides, along with other components, in the compositions. The combinations, as described above, can result in, for example, novel blends, mixtures, and other combinations that include, but are not limited to, copolymers such as, for example, in-chain and pendant copolymers.

Copolymers can be designed to perform in a desired manner in the biological organism. For example, copolymers can offer stability in performance, since some blends and mixtures can include agents that will leach at a rate that is faster than desired. An example of a composition that is improved through copolymerization is the combination of PEG with a polymer. While not intending to be bound by any theory or mechanism of action, the formation of copolymers can prevent the formation of discrete phases by a phase separation that may otherwise occur in such a blend or mixture of hydrophobic and hydrophilic materials, allowing for a much higher concentration of a component such as, for example, PEG, to be added to a p(HA-EA) to obtain a desired property. Phase separation morphologies can lead to a fast drug release and/or poor mechanical properties.

In some embodiments, the compositions of the present invention can be designed for a predetermined degree of crystallinity that can be reproducible. While not intending to be bound by any theory or mechanism of action, the degree of crystallinity can affect the water swelling and hydrolytic lability of a polymer, thus affecting the bioadsorption rate and rate of release of an agent. In other embodiments, the compositions of the present invention can be designed to exhibit surface erosion rather than bulk erosion in order to, for example, provide a product, such as an agent-releasing stent or coating that may be considered more desirable in some applications.

A polymer of the present invention can comprise a polymeric carrier having an A-moiety (A), a B-moiety (B), and an optional linkage ($L_1$) connecting A to B. The polymeric carrier may further comprise an agent (X), and a linkage ($L_2$) connecting X to the polymer. The p(HA-EA)-agent combination can be generally represented by formula (I):

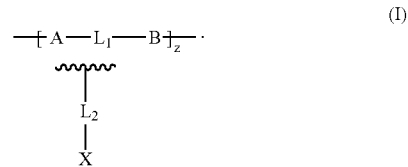

In formula (I), the A:B ratio can be less than, greater than, or equal to one; both A and B can be independently selected, and comprise any combination of monomers such that the polymer has at least one hydroxyalkanoate group and at least one ester amide group. At least one of $L_1$, B, $L_2$ or X is optional and may comprise an agent that is bioactive and/or biobeneficial, wherein the agent also affects a physical property and/or a mechanical property of a composition comprising the polymer. The integer z reflects the molecular weight of the polymer and depends upon the composition of the polymer, which varies according to the characteristics of the polymer that are desired. In some embodiments, the molecular weight of the polymer can range from about 40,000 Daltons to about 250,000 Daltons, from about 50,000 Daltons to about 200,000 Daltons, from about 75,000 Daltons to about 150,000 Daltons, from about 55,000 Daltons to about 95,000 Daltons, and any range therein.

In some embodiments, A can be represented by formula (II):

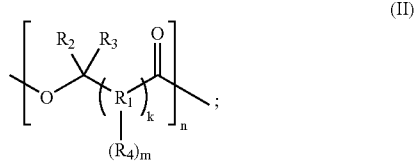

wherein the groups $R_1$ through $R_4$; k and m are integers, and n is an integer not equal to zero; and $L_1$, B, $L_2$, and X can include any polymer, agent, or combination described above. In some embodiments, at least one of $L_1$, B, $L_2$ or X should include an agent that is bioactive and/or biobeneficial, and the agent should also affect a physical property and/or a mechanical property of a composition comprising the polymer. Such an agent can also be included as a blend or mixture with a p(HA-EA) composition.

In some embodiments, the composition can comprise 3-hydroxybutyrate, 4-hydroxybutyrate, 3-hydroxyvalerate, 3-hydroxybutyrate-co-valerate, caprolactone, lactice, glycolide, lactide-co-glycolide, and combinations thereof. In other embodiments, each $R_1$ can be independently selected from alkylenes, alkanoates, alkyl alkanoates, diesters, acylals, diacids, saturated fatty acids, glycerides, and combinations thereof, provided that there is at least one hydroxyalkanoate unit within the PHA composition after the selection of $R_1$. In some embodiments, the molar percent of the hydroxyalkanoate component in the polymer is of an amount sufficient to produce a polymer with a characteristic that is indicative of a poly(hydroxyalkanoate). The integer k can be selected to obtain this design characteristic.

In some embodiments, the characteristics that may be tested include, but are not limited to, biological characteristics, chemical characteristics and mechanical characteristics. Biological characteristics include, but are not limited to, biodegradability and biocompatibility. Chemical characteristics include, but are not limited to, spectral behavior when analyzed using continous-wave or Fourier transform analyses such as, for example, Fourier transform infrared analysis (FTIR), Fourier transform nuclear magnetic resonance (FT-NMR); thermal behavior when analyzed using, for example, thermogravimetry, differential scanning calorimetry (TGA/DSC) and dynamic mechanical analysis (DMA); and surface behavior when analyzed using, for example, electron spectroscopy for chemical analysis (ESCA), secondary ion mass spectrometry (SIMS), scanning tunneling microscopy (STM), scanning force microscopy (SFM) using an atomic force microscope (AFM), and contact angle. Thermo-mechanical characteristics include, but are not limited to, tensile strength, tear strength, modulus, impact resistance (toughness), strain-to-failure, melting point, degree of crystallinity, and glass transition temperature ($T_g$).

In some embodiments, the molar percent of the hydroxyalkanoate component should range from about 40% to about 100%, from about 40% to about 95%, from about 40% to about 90%, from about 40% to about 85%, from about 40% to about 80%, from about 40% to about 75%, from about 40% to about 70%, from about 40% to about 65%, from about 40% to about 60%, or any range therein. In other embodiments, the molar percent of the PHA component should range from about 45% to about 100%, from about 50% to about 95%, from about 55% to about 90%, from about 60% to about 85%, from about 60% to about 80%, from about 60% to about 75%, from about 70% to about 100%, from about 70% to about 95%, from about 75% to about 95%, or any range therein. In other embodiments, the mass percent of the hydroxyalkanoate component should range from about 5% to about 85%, from about 10% to about 75%, from about 15% to about 65%, from about 20% to about 55%, from about 30% to about 50%, or any range therein. In other embodiments, the hydroxyalkanoate component ranges from about 20% to about 40%, and the ester amide component ranges from about 60% to about 80%. In other embodiments, the hydroxyalkanoate component ranges from about 60% to about 80%, and the ester amide component ranges from about 20% to about 40%.

In other embodiments, each $R_1$ can be independently selected from alkylenes, alkanoates, alkyl alkanoates, diesters, acylals, diacids, saturated fatty acids, glycerides, and combinations thereof, provided that there is at least one persistence length of hydroxyalkanoate components, wherein a persistence length is a maximum length scale beyond which a chain of hydroxyalkanoates is thought to begin losing rigidity. The persistence length is a measure that suggests, inter alia, the radius of gyration and entanglement potential of a polymer. In some embodiments, the persistence length ranges from about 0.5 nm to about 200 rn, from about 0.75 nm to about 150 nm, from about 1.0 nm to about 100 nm, from about 1.0 nm to about 75 nm, from about 1 nm to about 50 nm, from about 1 nm to about 25 rn, and any range therein. The radius of gyration of a polymer in solution can be measured using viscosity or size-exclusion chromatography.

In other embodiments, each $R_1$ can be independently selected from alkylenes, alkanoates, alkyl alkanoates, diesters, acylals, diacids, saturated fatty acids, glycerides, and combinations thereof, provided that there is at least an oligomer of hydroxyalkanoate repeating units present within the polymer, wherein an oligomer ranges in length from about 4 units to about 20 units, from about 6 units to about 20 units, from about 8 units to about 20 units, or any range therein.

The functional groups $R_2$ through $R_4$ can comprise any functional group or agent taught herein. In some embodiments, the functional groups present in a p(HA-EA) composition such as, for example, $R_2$ through $R_4$, can be used to attach an agent covalently or non-covalently; provide crosslinking sites; assist in biodegradation of a p(HA-EA) by serving as an electron donating or withdrawing moiety; decrease immunogenicity; modify pharmacokinetics and pharmacodynamics such as the targeting of polymer fragments that may comprise agents, the solubility and bioavailability of polymer fragments and agents; and combinations thereof. In some embodiments, $R_2$ through $R_4$ can be independently selected from hydrogen; substituted, unsubstituted, hetero-, straight-chained, branched, cyclic, saturated and unsaturated aliphatic radicals; and substituted, unsubstituted, and hetero-aromatic radicals. The integer m is limited by the integer k, can be selected to modify the characteristics of the polymer to a predetermined degree, and can vary according to the type and variety of functional groups that have been selected to meet particular design considerations in the development of the polymer.

In other embodiments, the functional groups that can be included in $R_2$ through $R_4$ contain oxygen-containing groups such as, for example, hydroxyls, carboxyls, alkoxyls, epoxyls, carbonyls, and combinations thereof. In other embodiments, the functional groups that can be included in $R_2$ through $R_4$ contain nitrogen-containing groups such as, for example, amino, amido, nitro, isocyanato, azido, diazo, hydrazino, azo, azoxyl, cyano, and combinations thereof. In other embodiments, the functional groups that can be included in $R_2$ through $R_4$ contain sulfur-containing groups such as, for example, thio, thiol, sulfide, and combinations thereof. In other embodiments, the functional groups that can be included in $R_2$ through $R_4$ contain ethylenically unsaturated groups such as, for example, vinyl, allyl, acryloyl and methacrylol, and maleate and maleimido.

In other embodiments, the functional groups that can be included in $R_2$ through $R_4$ contain ethers, esters, orthoesters; anhydrides, ketones, urethanes, halogens, and combinations thereof. In all embodiments, the functional groups included in $R_2$ through $R_4$ may be any functional group taught herein, may likewise be substituted by any functional group taught herein, and may also contain a heteroatom. Examples of heteroatoms include, but are not limited to, sulfur, phosphorous, oxygen, nitrogen and combinations thereof.

In some embodiments, the optional linkage $L_1$ can comprise a substituted, unsubstituted, hetero-, straight-chained, branched, cyclic, saturated or unsaturated aliphatic radical; and a substituted or unsubstituted aromatic radical. In other embodiments, $L_1$ can comprise from about 0 to about 50 carbon atoms, from about 2 to about 40 carbon atoms, from about 3 to about 30 carbon atoms, from about 4 to about 20 carbon atoms, from about 5 to about 10 carbon atoms, and any range therein.

In other embodiments, the $L_1$ can comprise a non-carbon species such as, for example, a disulfide. In other embodiments, $L_1$ can comprise poly(vinyl pyrrolidone); carboxymethylcellulose; poly(ethylene); polypropylene; hyaluronic acid; heparin; poly(styrene sulfonate); phosphorylcholine; substituted methacrylates; substituted or unsubstituted poly(alkylene glycols), which include, but are not limited to, PEG, PEG derivatives such as mPEG, amino-terminated PEG, carboxyl-terminated PEG, and any other functionalized PEGs available in the art; PPG, poly(tetramethylene glycol), poly(ethylene oxide-co-propylene oxide), poly(ethylene glycol-co-hydroxybutyrate), or copolymers and combinations thereof. In one embodiment, the poly(alkylene glycol) is PEG. In another embodiment, the poly(alkylene glycol) may comprise a PEG derivative such as amino-terminated PEG. In another embodiment, $L_1$ can comprise a co-polymer of PEG or a PEG derivative. In another embodiment, $L_1$ can comprise a co-polymer of PEG and heparin, a copolymer of PEG and hirudin, or combination thereof.

In other embodiments, the optional linkage $L_2$ can be used to connect X to the polymer. The agent X can be connected to the polymer by $L_2$, which can be any interunit linkage. In some embodiments, $L_2$ can be an ether, an amide, an ester, an anhydride, an orthoester, an all-aromatic carbonate, an acetal, a ketal, a urethane, a urea, a glycoside, a disulfide, a siloxane linkage, or a combination thereof. It is to be appreciated that some of these linkages may not be used in some embodiments of the present invention.

The selection of $L_2$ allows for control of the relative strength or stability of the bond between X and the polymeric carrier as compared to the strength or stability of the bonds within the polymeric carrier. Such control allows for a controlled release of agents that are substantially free of attached molecules from the polymeric carrier. The agent X can be biobeneficial, bioactive, diagnostic, plasticizing, or a have a combination of these properties.

In some embodiments, $L_1$, B, $L_2$, X, or a combination thereof, can include a polyol, a polycarboxylic acid, an amino acid, or a combination thereof. These moieties can be incorporated into a p(HA-EA) to provide a desired chemical functionality for linking an agent; and/or, provide a desired physical/mechanical, bioactive or biobeneficial characteristic; or a combination thereof. The polyols used in the present invention may be organic compounds having two or more hydroxyl groups. In some embodiments, the polyols include, but are not limited to, cyclohexanedimethanol, glycerol, trimethylolpropane, pentaerythritol and compounds represented by formula (III):

wherein R can be a substituted, unsubstituted, hetero-, straight-chained, branched, cyclic, saturated or unsaturated aliphatic radical; or a substituted, unsubstituted, or hetero- aromatic radical; and i is an integer.

In some embodiments, the polyols are diols. Examples of diols that can be used include ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, dihydroxyacetone, serinol, and cyclohexanedimethanols such as, for example, 1,4-cis-cyclohexanedimethanol. In other embodiments, the diols can be aromatic diols such as, for example, 1,4-benzenedimethanol (also known as p-phenylene dicarbinol or as p-xylene-α,α'-diol). In other embodiments, polyols such as glycerol, trimethylolpropane, pentaerythritol and sorbitol are useful as long as the possibility of forming a crosslink is considered. Polyols can be selectively polymerized by protecting one or more groups to prevent crosslinking, intentionally forming a crosslink, or using chemistry that is selective for particular reactive groups. In other embodiments, functional diols such as serinol and diacetone alcohol can also be used.

In other embodiments, R can be a substituted or unsubstituted poly(alkylene glycol), which includes, but are not limited to, poly(ethylene glycol) (PEG); a functionalized PEG such as, for example, amino-terminated PEG; PPG; poly(tetramethylene glycol); poly(ethylene oxide-co-propylene oxide); poly(ethylene glycol-co-hydroxybutyrate); or copolymers and combinations thereof It is to be appreciated that one skilled in the art should recognize that some of the groups, subgroups, and individual polyols may not be used in some embodiments of the present invention.

The PEGs can have molecular weights ranging from about 400 Daltons to about 40,000 Daltons, from about 200 Daltons to about 20,000 Daltons, from about 400 Daltons to about 25,000 Daltons, from about 400 Daltons to about 15,000 Daltons, from about 500 Daltons to about 10,000 Daltons, from about 750 Daltons to about 7500 Daltons, from about 1000 Daltons to about 10,000 Daltons, from about 1000 Daltons to about 5000 Daltons, or any range therein. The molecular weights are taught herein as a number average molecular weight.

The polycarboxylic acids used in the present invention may be organic acids having two or more carboxyl groups. In some embodiments, the polycarboxylic acids include dicarboxylic acids and tricarboxylic acids and may be aliphatic or aromatic structures. In one embodiment, the polycarboxylic acids are represented by formula (IV):

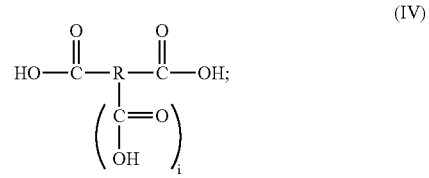

wherein R is optional and can be a substituted, unsubstituted, hetero-, straight-chained, branched, cyclic, saturated or unsaturated aliphatic radical; and a substituted or unsubstituted aromatic radical; and i is an integer.

Examples of polycarboxylic acids include, but are not limited to, oxalic acid, malonic acid, succinic acid, glutaric acid, adipic acid, pimelic acid, suberic acid, sebacic acid, azelaic acid, terephthalic acid, citric acid, maleic acid, fumaric acid and combinations thereof. It is to be appreciated that one skilled in the art should recognize that some of the groups, subgroups, and individual polycarboxylic acids may not be used in some embodiments of the present invention.

In some embodiments, R is a methylene [—$CH_2$)$_y$—] or phenylene group [—$C_6H_4$—], where y is an integer between 0 and 16. In other embodiments, R can include a substituted or unsubstituted poly(alkylene glycol), which includes, but is not limited to, PEG, PEG derivatives such as amino-terminated PEG and carboxyl-terminated PEG; PPG; poly(tetramethylene glycol); poly(ethylene oxide-co-propylene oxide); poly(ethylene glycol-co-hydroxybutyrate); or copolymers and combinations thereof. In other embodiments R can be aryl. In other embodiments, R can be substituted with an epoxy group.

In other embodiments, the aromatic dicarboxylic acids can be an isomer of phthalic acid such as, for example, terephthalic acid, isophthalic acid, phthalic acid, and combinations thereof. In other embodiments, the phenyl ring of the aromatic dicarboxylic acid can be substituted with other groups such as alkyl groups, alkoxy groups, halogen groups, and any other functional groups defined above that will not interfere with the polymerization.

In some embodiments, the polyols and polycarboxylic acids can be used to crosslink the p(HA-EA)s of the present invention. In one example, the p(HA-EA)s are combined with an excess of one or more diacids to provide carboxyl-terminated p(HA-EA)s that can then be combined with diols to crosslink the p(HA-EA)s. In these embodiments, the crosslinked p(HA-EA)s can serve as a network for the covalent or non-covalent attachments of agents, where the non-covalent attachment can be, inter alia, a physical entrapment or physical entanglement of an agent in the crosslinked network.

As with the polyols, care must be taken to control crosslinking when using polycarboxylic acids to produce the polyesters of the present invention, because crosslinking can produce a polymer that has a high viscosity, is gelled, or is otherwise difficult to process. In some embodiments, crosslinking can be controlled by selecting polycarboxylic acids that contain carboxyl groups with different reactivities. In other embodiments, crosslinking can be controlled by stoichiometry or by having an excess of one reactant. In other embodiments, crosslinking can be controlled by protecting one or more of the carboxyl groups with a chemical moiety, such as, for example, by forming benzyl esters. In some embodiments, the polycarboxylic acids include, but are not limited to, 1,3,5-benzenetricarboxylic acid, tricarballylic acid, trimellitic acid and trimellitic anhydride. For example, combining trimellitic anhydride in a reaction with one equivalent of an amine or hydroxy functional compound can essentially functionalize, or protect, one of the carboxyl groups.

The amino acids used in the present invention may be organic compounds comprising an amino group and a carboxyl group, and the amino group may be primary or secondary. Examples of amino acids include, but are not limited to, glycine, alanine, valine, leucine, isoleucine, methionine, phenylalanine, tyrosine, aspartic acid, glutamic acid, lysine, arginine, serine, threonine, cysteine, asparagine, proline, tryptophan, histidine and combinations thereof. In some embodiments, the amino acids are represented by formula (V):

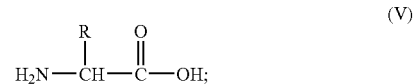

wherein R may be a hydrogen; a substituted, unsubstituted, hetero-, straight-chained, branched, cyclic, saturated or unsaturated aliphatic radical; or a substituted, unsubstituted, or hetero- aromatic radical. In some embodiments, R can be substituted, unsubstituted, or hetero- forms of methyl, iso-propyl, sec-butyl, iso-butyl, benzyl, or a combination thereof.

In embodiments where R is substituted, examples of substitutents include, but are not limited to, hydroxyl, carboxyl, amino, imino groups and combinations thereof. In embodiments where R is heteroaliphatic, examples of heteroatoms include, but are not limited to, sulfur, phosphorous, oxygen, nitrogen and combinations thereof In other embodiments, R can comprise substituted or unsubstituted poly(alkylene glycols), which include, but are not limited to, PEG, PEG derivatives such as mPEG, PPG, poly(tetramethylene glycol), poly(ethylene oxide-co-propylene oxide), poly(ethylene glycol-co-hydroxybutyrate), or copolymers and combinations thereof.

In some embodiments, the amino acids may be limited to bifunctional amino acids or trifunctional amino acids. In other embodiments, the amino acids may be limited to diamines or triamines. In other embodiments, the amino acids may be limited to monocarboxylics or dicarboxylics. In other embodiments, the amino acids may be limited to aliphatics. In other embodiments, the amino acids may be limited to aromatics. In other embodiments, the amino acids may be limited to amides. It is to be appreciated that one skilled in the art should recognize that some of the groups, subgroups, and individual amino acids may not be used in some embodiments of the present invention.

In other embodiments, $L_1$, B, $L_2$ and/or X can include any one or any combination of formulas (VI)-(VIII):

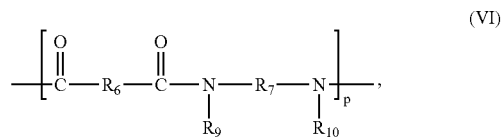

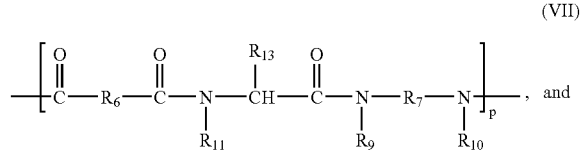

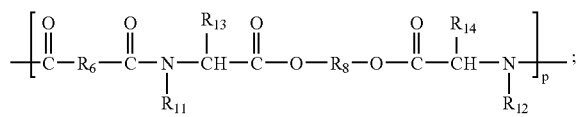

(VIII)

where (a) $R_6$ can be optional and can also be independently selected from a substituted, unsubstituted, hetero-, straight-chained, branched, cyclic, saturated or unsaturated aliphatic radical; or a substituted, unsubstituted, or hetero-aromatic radical; (b) $R_7$ and $R_8$ can be independently selected from a substituted, unsubstituted, hetero-, straight-chained, branched, cyclic, saturated or unsaturated aliphatic radical; or a substituted, unsubstituted, or hetero-aromatic radical; (c) $R_9$ through $R_{12}$ can be independently selected from a hydrogen; a substituted, unsubstituted, hetero-, straight-chained, branched, cyclic, saturated or unsaturated aliphatic radical; or a substituted, unsubstituted, or hetero-, aromatic radical; (d) $R_{13}$ and $R_{14}$ can be independently selected from a hydrogen; a substituted, unsubstituted, hetero-, straight-chained, branched, cyclic, saturated or unsaturated aliphatic radical; and a substituted or unsubstituted aromatic radical. In some embodiments, $R_7$ is not a substituted, unsubstituted, or hetero-aromatic radical.

In some embodiments using formulas (I), (II) and (VI)-(VIII), m can range from about 0 to about 50, from about 1 to about 40, from about 2 to about 30, from about 3 to about 20, from about 4 to about 10, or any range therein; n can range from about 1 to about 1400, from about 10 to about 800, from about 20 to about 400, or any range therein; p can range from about 4 to about 1400, from about 10 to about 800, from about 20 to about 400, or any range therein; and z can range from about 10 to about 1600, from about 20 to about 1200, from about 30 to about 900, from about 50 to about 600, or any range therein; and the sum of n and p and can range from about 30 to about 1600, from about 50 to about 1200, from about 75 to about 900, from about 100 to about 600, or any range therein. Generally speaking, the heterogenous nature of the terminal groups on the hydroxyalkanoates can be altered to make the terminal groups uniform such that the polymeric reaction products are more predictable and controllable. In some embodiments, for example, the hydroxyalkanoates can be carboxyl-terminated, hydroxyl-terminated, or amino-terminated.

In some embodiments, the hydroxyalkanoates can be altered to be carboxyl-terminated, for example, by combining the hydroxyalkanoates with diacids. In other embodiments, the hydroxyalkanoates can be altered to be hydroxyl-terminated, for example, by combining the hydroxyalkanoates with diols. In other embodiments, the hydroxyalkanoates can be altered to be amino-terminated, for example, by combining a hydroxyl-terminated hydroxyalkanoate with reactive amine-containing moieties or reactive moieties that can be converted to amines. In one example, a hydroxyl-terminated hydroxyalkanoate can be combined with aziridine to create an amine-terminated hydroxyalkanoate. In another example, a hydroxyl-terminated hydroxyalkanoate can be combined with a diisocyanate to form an isocyanate-terminated hydroxyalkanoate that can be combined, for example, with water to produce an amine-terminated hydroxyalkanoate. In another example, a hydroxyl-terminated hydroxyalkanoate can be combined with tosyl chloride to form a tosyl-terminated hydroxyalkanoate that can be combined, for example, with ammonia to displace the tosyl moiety and produce an amino-terminated hydroxyalkanoate. These alterations can be performed on poly(hydroxyalkanoates) as well, and one of skill in the art can select the reaction conditions necessary to obtain the desired reaction products.

In some embodiments, the polymers of the present invention can be prepared in the following manner: a poly (hydroxyalkanoate) can be combined with a multi-functional amino acid, a diacid or derivative of a diacid, and an agent. In embodiments where the incorporation of a peptide-type combination is desired, two amino acids can be independently selected and combined such as, for example, where one amino acid is bi-functional and the other is multi-functional.

An example of a multi-functional amino acid is a tri-functional amino acid. Examples of tri-functional amino acids include, but are not limited to, lysine, tyrosine, arginine, or glutamic acid. Examples of diacids include, but are not limited to, the dicarboxylic acids listed above. Examples of derivatives of diacids include, but are not limited to, diacid chloride, a dianhydride, or a di-p-nitrophenyl ester. In the event that a dicarboxylic acid is used, the reaction may be carried out in the presence of 1-ethyl-3(3-dimethylaminopropyl) carbodiimide (EDC) or 1,3-dicyclohexylcarbodiimide (DCC) in a solvent such as dimethylformamide (DMF) or tetrahydrofuran (THF). If a diacid chloride or di-p-nitrophenyl ester is used, an excess of pyridine or triethylamine should be present. Examples of other solvents that may be used include, but are not limited to, dimethylacetamide (DMAC), dimethylsulfoxide (DMSO), acetone, and dioxane.

The reaction conditions used in preparing the PEAs copolymer segments, such as those in formulas (VI)-(VIII), should be anhydrous and favor esterification. In some embodiments, the reaction solvents can include toluene and benzene and should be distilled to remove water. The reaction can be catalyzed by a strong acid or base such as, for example, p-toluenesulfonic acid (TsOH). In some embodiments, the temperature of the reaction ranges from about 25° C. to about 150° C., from about 35° C. to about 100° C., from about 50° C. to about 80° C., or any range therein. In some embodiments, the reaction times range from about 1 hour to about 24 hours, from about 6 hours to about 18 hours, from about 10 hours to about 14 hours, or any range therein. Any agent described above can be used.

Trifunctional amino acids can be incorporated into the polymer by protecting the third functionality with a protecting group that is later removed. Examples of protecting groups are benzyl esters for the lysine carboxyl or t-butoxycarbonyl for amino groups such as, for example, the amino group in glutamic acid.

The benzyl ester protecting group may be removed from the lysine carboxyl by hydrogenolysis with hydrogen gas over a catalyst such as, for example, palladium or platinum on carbon. Examples of suitable solvents include, but are not limited to, ethanol, methanol, isopropanol, and THF. In some embodiments, the reaction may be conducted under about 1 atm of hydrogen for about 6 hours to about 24 hours, for about 8 hours to about 16 hours, for about 10 hours to about 14 hours, or any range therein. After removal of the protecting group, an agent comprising an amino, a hydroxyl, a thiol, or a combination thereof can be connected to the carboxyl group. Coupling agents used to connect the agent include, but are not limited to, EDC and DCC. Thionyl chloride or phosphorous pentachloride may be used in a less selective process of preparing the acid chloride derivative.

An amine functional compound such as, for example, 4-amino-TEMPO, may be connected to a polymer containing free carboxyls such as, for example, the lysine-derived carboxyls, by first activating the carboxyls and coupling the amine in a solvent under agitation. The carboxyls may be activated with, for example, N-hydroxysuccinimide (NHS) and DCC in a solvent such as, for example, THF or chloroform, which produces N-hydroxysuccinimidyl ester. Examples of the solvent that may be used to couple the amine to the carboxyls include, but are not limited to, THF and DMF. In some embodiments, the reaction occurs at a temperature ranging from about 5° C. to about 50° C., from about 15° C. to about 35° C., from about 20° C. to about 30° C., or any range therein. In some embodiments, the reaction time ranges from about 0.5 hours to about 24 hours, from about 1 hour to about 18 hours, from about 4 hours to about 16 hours, from about 6 hours to about 12 hours, or any range therein.

The PEAs can be combined with hydroxyalkanoates to produce copolymers that are in-chain and/or pendant in the p(HA-EA compositions. One purpose for adding PEA functionality is to make a p(HA-EA) composition that is pro-healing, tougher, and that has a higher impact resistance and lower modulus. Such a p(HA-EA) composition may be more applicable to particular applications such as, for example, drug-eluting stents. Another purpose for adding PEA functionality to a p(HA-EA) composition is to introduce an additional control over in vivo biodegradation rates and products. As the amount of PEA increases in the polymer, the amount of enzymatic hydrolysis that occurs in the composition in vivo increases as well, thus providing another mechanism of chain scission that is controllable based on the design of the composition.

In some embodiments, a family of p(HA-EA)s can be represented by formula (IX):

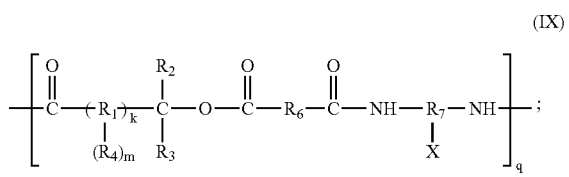

(IX)

wherein the groups $R_1$ through $R_7$, k, m, and X are defined above; and q is an integer not equal to zero. In one embodiment, $R_7$ can be a carboxyl-terminated alkylene radical in an amino acid, such as, for example lysine.

In other embodiments, a family of p(HA-EA)s can be represented by formula (X):

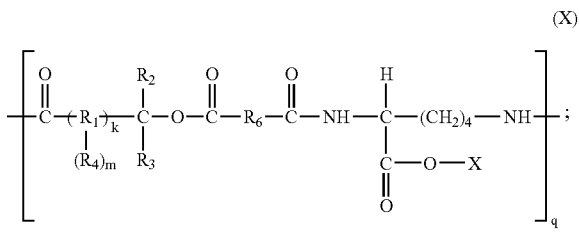

(X)

wherein the groups $R_1$ through $R_6$, k, m, and X are defined above; and q is an integer not equal to zero. In one embodiment, $R_7$ can be a carboxyl-terminated alkylene radical in an amino acid, such as, for example lysine.

In another embodiment, a family of p(HA-EA)s comprising a dipeptide fragment can be represented by formula (XI):

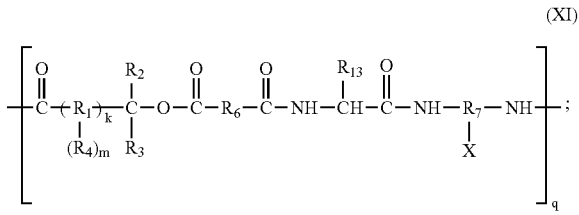

(XI)

wherein the groups $R_1$ through $R_7$, $R_{13}$, k, m, and X are defined above; and q is an integer not equal to zero. In one embodiment, $R_7$ can be a carboxyl-terminated alkylene radical in an amino acid, such as, for example lysine.

In another embodiment, a family of p(HA-EA)s can be represented by formula (XII):

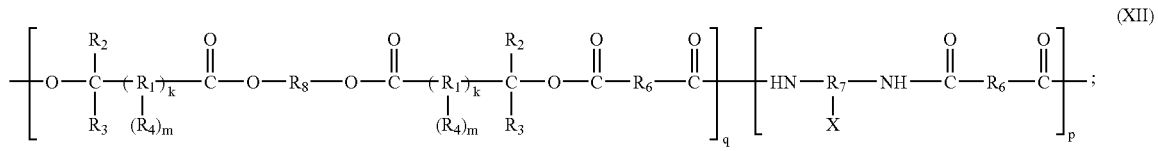

(XII)

wherein the groups $R_1$ through $R_8$, k, m, p, and X are defined above;. In one embodiment, $R_7$ can be a carboxyl-terminated alkylene radical in an amino acid, such as, for example lysine.

In another embodiment, a family of p(HA-EA)s can be represented by formula (XIII):

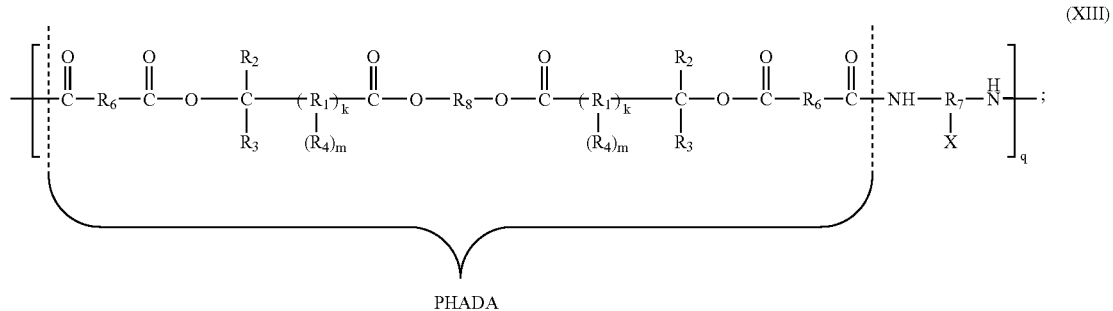

(XIII)

PHADA wherein the groups $R_1$ through $R_8$, k, m, and X are defined above; and q is an integer not equal to zero. In one embodiment, $R_7$ can be a carboxyl-terminated alkylene radical in an amino acid, such as, for example lysine. In another embodiment, $R_6$ can be independently selected as an alkylene radical such as, for example, an ethylene radical. The main portion of this polymer is a poly (hydroxyalkanoate diacid)("PHADA"). Accordingly, formula (XIII) can be combined, for example, with formulas (VI)-(VIII) to produce a family of polymers that can include, but is not limited to, formula (XIV):

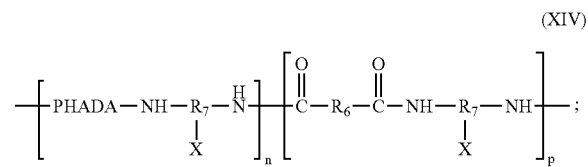

(XIV)

wherein $R_6$, $R_7$, p and X are defined above; and q is an integer not equal to zero. In some embodiments, $R_7$ can be a carboxyl-terminated alkylene radical in an amino acid, such as, for example lysine.

In another embodiment, a family of p(HA-EA)s comprising amino-terminated hydroxyalkanoates can be represented by the formula (XV):

thereof. In other embodiments, $R_{15}$ can be an ethylene radical. In one embodiment, $R_7$ can be a carboxyl-terminated alkylene radical in an amino acid, such as, for example lysine. In another embodiment, $R_6$ can be independently selected as an alkylene radical such as, for example, an ethylene radical.

A variety of moieties, including the agents described above, can be attached pendant and/or in-chain with the p(HA-EA)s of the present invention as follows:

I. Agents Attached Pendant to the Polymer

Agents can be attached to any of the polymers taught herein in a variety of ways. For example, the agents can be connected covalently or non-covalently such as, for example, by ionic attachment, hydrogen bonding, metal ion coordination, or physical interlinking. In some embodiments, the A, $L_1$, B, $L_2$, and/or X can be chemically functionalized to provide sites for connecting agents as pendant groups to the p(HA-EA) compositions. Examples of functional groups that can be used in forming the connections are described above.

In some embodiments, the functional groups introduced to A, $L_1$, B, $L_2$, and/or X include, but are not limited to, carboxylic acids, amines, thiols, alcohols, anhydrides, esters, unsaturated groups and halogens. In other embodiments, metals can be introduced as functional groups for linking agents to polymers. In other embodiments of the present invention, diacids comprising epoxy groups may be

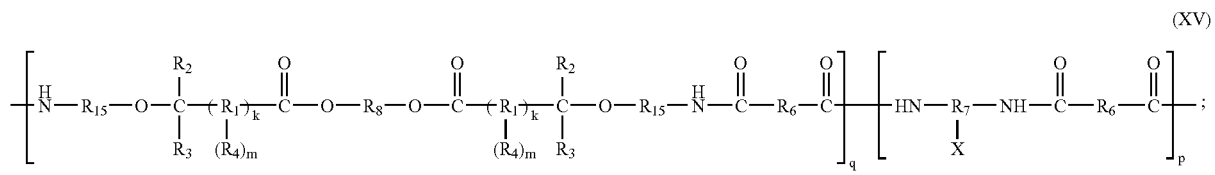

(XV)

wherein the groups $R_1$ through $R_8$, k, m, p and X are defined above; and q is an integer not equal to zero. The group $R_{15}$ is part of the moiety used to create an amino-terminated hydroxyalkanoate. In some embodiments, $R_{15}$ can be an alkylene, an amide, an acyl or a combination included in the p(HA-EA)s as highly-strained reactive groups that can be used to connect agents to the polymer. Examples of such p(HA-EA)s may include, but are not limited to, 2,3-epoxysuccinic acid, 3,4-epoxyadipic acid or a diepoxyadipic acid.

Surface treatments can be used to functionalize the polymer surface and include, for example, chemical, mechanical, and combined chemical and mechanical treatments, which are known to one of skill in the art. Mechanical surface treatment includes, but is not limited to, abrading, polishing, and applying laser energy to a surface. Laser surface treatment includes applying laser energy to heat, oxidize, pyrolyze, activate, or cleave chemical bonds. Chemical surface treatment includes, but is not limited to, etching such as, for example, chromic acid etching; ozonation; iodine treatment; sodium treatment; surface grafting; anodizing; thermal, flame, UV, corona discharge, and plasma treatments; and the use of primers. In some embodiments, medical articles may be surface treated after they have been formed, which can reduce problems that may be associated with using functionalized p(HA-EA)s to form a medical article. In some embodiments, such treatments can be used to localize the functional groups to predetermined regions on a polymer surface and allow for localization of select agents.

In some embodiments, the surface treatment comprises chromic acid etching to introduce functional groups such as, for example, hydroxyl, carbonyl, carboxylic acid, and —$SO_3H$ groups and form root-like cavities which provide sites for mechanical interlocking. In other embodiments, the surface treatment comprises applying a more aggressive etching solution containing, for example, a sodium-naphthalene complex dissolved in tetrahydrofuran or a sodium-ammonia complex dissolved in ammonia to introduce unsaturated bonds, carbonyl groups, and carboxyl groups. In other embodiments, the surface treatment comprises iodine treatment to alter the crystallinity of the polymer surface from an alpha form (where the N—H groups lie parallel to the surface) to a beta form (where the N—H groups stand perpendicular to the surface). In other embodiments, the surface treatment comprises application of a primer, which is typically a multifunctional chemical, to act as a chemical bridge between the polymer and an agent.

In some embodiments, the surface treatment comprises surface grafting a chemical to a polymeric surface to provide functional groups for attachment of an agent such as, for example, exposing a poly(ethylene) to gamma radiation in the presence of a vinyl acetate monomer to chemically graft the vinyl acetate monomer on the poly(ethylene) surface. In other embodiments, the surface treatment comprises plasma treatment with ions of a gas such as, for example, Ar, He, $N_2$, $O_2$, air, and $NH_3$ to introduce functional groups such as, for example, carboxylic or amino groups. In other embodiments, the surface treatment comprises a corona discharge, usually in the presence of air and at atmospheric pressure, to introduce functional groups such as, for example, carbonyl, hydroxyl, hydroperoxide, aldehyde, ether, ester, and carboxylic acid groups, as well as unsaturated bonds.

In some embodiments, the surface treatment comprises flame treatment to oxidize the polymer surface and introduce functional groups such as, for example, hydroxyl, carbonyl, carboxyl, and amide groups through a free radical mechanism. In other embodiments, the surface treatment comprises thermally treating a polymeric surface to a blast of hot air (approximately 500° C.) to create functional groups such as, for example, carbonyl, carboxyl, amide, and hydroperoxide groups through a free radical mechanism. In other embodiments, the surface treatment comprises applying ultraviolet (UV) radiation with high intensity UV light of a predetermined wavelength to create functional groups, where the process may use, for example, a wavelength of 184 nm to crosslink the surface of a polyethylene or a wavelength of 253.7 nm to avoid cross-linking and induce hydrogen bonding. In other embodiments, the surface treatment comprises abrading or polishing the polymer surface in the presence of an agent to create free radicals that react directly with the agent.

The selection of functional groups for connecting an agent to a polymer will affect the ability of the agent to release from the polymer in vivo. In formula (X), for example, $L_2$ is an ester, which may be undesirable in some embodiments. As illustrated and described below, the careful selection of $L_2$ can help alleviate safety and regulatory issues that may arise from the creation of derivatives of X during biodegradation of the polymers.

Examples of $L_2$ include, but are not limited to, amides, ureas, urethanes, esters, semicarbazones, imines, oximes, anhydrides, ketals, acetals, orthoesters, disulfides, and all-aromatic carbonates. In some embodiments, $L_2$ can be an ester, an anhydride, a ketal, an acetal, an orthoester, or an all-aromatic carbonates. In some embodiments, $L_2$ can be an anhydride, a ketal, an acetal, an orthoester or an all-aromatic carbonate. In some embodiments, $L_2$ can be a ketal, an acetal, an orthoester or an all-aromatic carbonate. In some embodiments, $L_2$ can be an acetal, an orthoester or an all-aromatic carbonate. In some embodiments, $L_2$ can be an orthoester or an all-aromatic carbonate. In some embodiments, $L_2$ can be an all-aromatic carbonate, which includes linkages comprising moieties represented by formula (XVI):

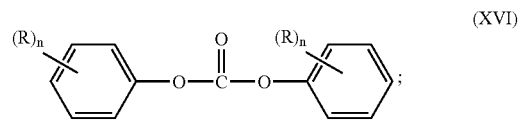

(XVI)

wherein R is optional and can be independently selected from, for example, a substituted, unsubstituted, hetero-, straight-chained, branched, cyclic, saturated and unsaturated aliphatic radicals; substituted and unsubstituted aromatic radicals; and combinations thereof. The subscript n is an integer.

In some embodiments, the p(HA-EA) is represented by formula (XVII):

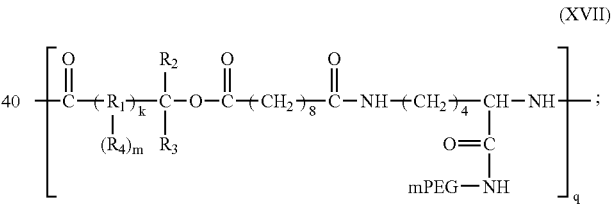

(XVII)

wherein $R_1$ through $R_4$, k, m, and q are defined above; and the number of ethylene oxide repeating units ranges from about 1 to about 100, from about 2 to about 80; from about 3 to about 70, from about 4 to about 60, from about 2 to about 20, from about 3 to about 30, from about 4 to about 40, from about 5 to about 50, and any range therein.

In formula (XVII), the diacid is sebacic acid, the amino acid is lysine, and the agent is PEG. The PEG is connected to the B-moiety through an amide linkage, which is a stable linkage relative to the stability of the remainder of the polymer. It should be appreciated that any PEG derivative such as, for example, mPEG can also be used.

Adding PEO functionality to a p(HA-EA) composition modifies the composition by, for example, increasing water uptake, which provides a plasticizing effect and makes the polymer more flexible to increase toughness. An increase in water uptake can also increase the hydrolysis rate and thereby provide an additional control over biodegradation and drug release rate. The PEG component may leach from a blend or mixture of PEG and p(HA-EA) at a rate faster than desired due to the relative hydrophilicity of the PEG phase in the blend or mixture. Copolymerization of a PEO functionality with the p(HA-EA) compositions will prevent such leaching by circumventing a phase separation that otherwise occurs in blends of hydrophobic and hydrophilic materials. The copolymers will allow for an increased loading concentration of the hydrophilic PEG moiety and sustain any improvements in mechanical and biobeneficial properties that are realized by the addition of the PEG.

In some embodiments, the p(HA-EA) is represented by the formula (XVIII):

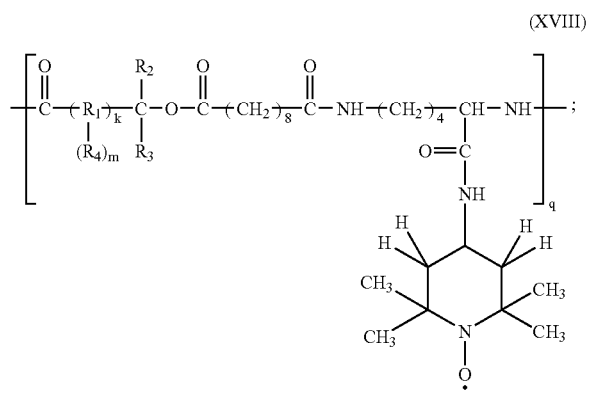

(XVIII)

wherein $R_1$ through $R_4$, k, m, and q are defined above.

In formula (XVIII), the diacid is sebacic acid, the amino acid is lysine, and the agent is 4-amino-2,2,6,6-tetramethylpiperidine-1-oxyl(4-amino-TEMPO). The 4-amino-TEMPO is connected to the B-moiety through an amide linkage, which may remain intact during biodegradation of the polymer resulting in attachment of additional molecules to the 4-amino-TEMPO that were derived from degradation of the polymer at the ester linkages. As a result, such a released agent would be a derivative of 4-amino-TEMPO rather than 4-amino-TEMPO and could cause regulatory concerns.

In some embodiments, the p(HA-EA) is represented by the formula (XIX):

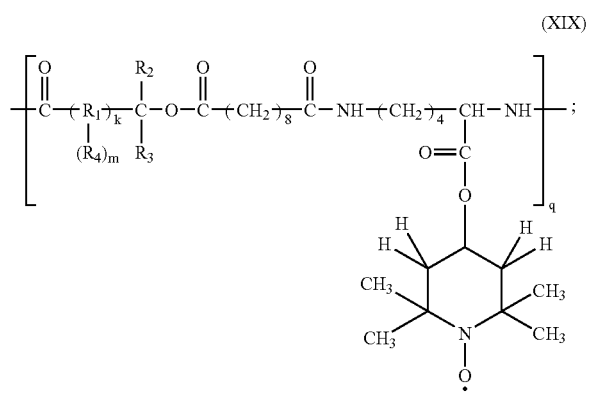

(XIX)

wherein $R_1$ through $R_4$, k, m, and q are defined above.

In formula (XIX), the diacid is sebacic acid, the amino acid is lysine, and the agent is 4-hydroxy-2,2,6,6-tetramethylpiperidine-1-oxyl(4-hydroxy-TEMPO). The 4-hydroxy-TEMPO is connected to the B-moiety through an ester linkage, which is more labile than an amide linkage and allows for release of the agent from the polymer. The cleavage of the $L_2$ ester competes with the cleavage of the PEA esters and may result in attachment of additional molecules to the 4-hydroxy-TEMPO that were derived from degradation of the polymer at ester linkages.

In some embodiments, the p(HA-EA) is represented by the formula (XX):

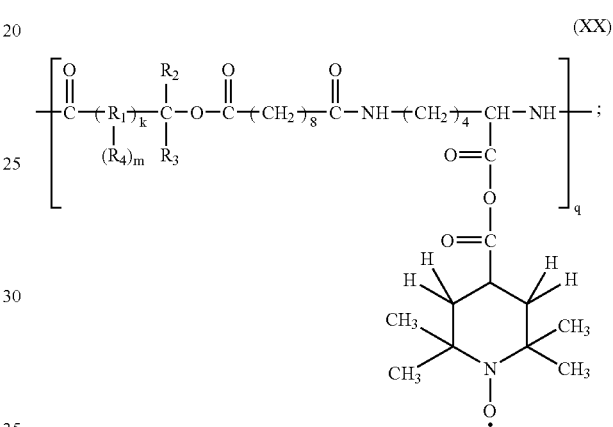

(XX)

wherein $R_1$ through $R_4$, k, m, and q are defined above.

In formula (XX), the diol is butane-1,6-diol, the diacid is sebacic acid, the amino acid is lysine, and the agent is 4-carboxy-2,2,6,6-tetramethylpiperidine-1-oxyl(4-carboxy-TEMPO). The 4-carboxy-TEMPO is connected to the B-moiety through an anhydride linkage, which is more labile than an ester linkage and, thus, may allow for release of the agent without attachment of additional molecules derived from biodegradation of the polymer at ester linkages.

In some embodiments, the p(HA-EA) is represented by formula (XXI):

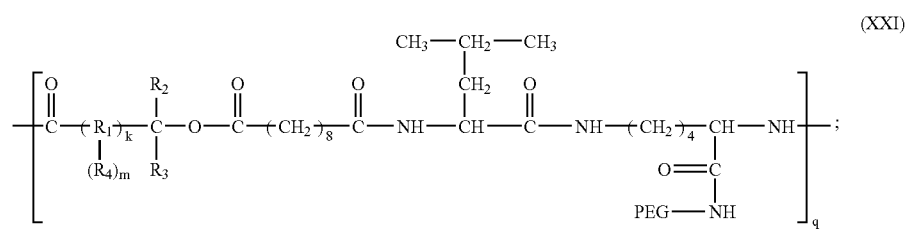

(XXI)

wherein $R_1$ through $R_4$, k, m, and q, and the number of ethylene oxide repeating units are defined above.

In formula (XXI) the diacid is sebacic acid, one amino acid is leucine, the other amino acid is lysine, X is PEG and $L_2$ is an amide, which is stable relative to the stability of the remainder of the polymer. It should be appreciated that any PEG derivative such as, for example, mPEG can also be used.

There are a variety of commercially available PEG molecular weights and derivatives that are designed for specific applications. In some embodiments, the PEG can be functionalized to allow attachment of the PEG to any functional group taught herein such as, for example, amine, thiol, hydroxyl and carboxyl functional groups. In these embodiments, the attachment of the PEG can be covalent, non-covalent, biodegradable or non-biodegradable. The PEGs may also be used as a point of attachment for carrying and/or delivering any other agents taught herein. In other embodiments, the PEG can be combined with the p(HA-EA) compositions in the form of a crosslinked hydrogel for the covalent attachment, non-covalent attachment, and the modulation of the delivery rates of agents. In other embodiments, the PEGs have a molecular weight of 30,000 Daltons or less, or can be biodegraded to fragments that have a molecular weight of 30,000 Daltons or less to ensure renal clearance from a subject.

In some embodiments, a p(HA-EA) is represented by formula (XXII):

p(HA-EA) can be reacted with the estradiol-DETOSU to form the PEA-agent combination.

A polymeric agent such as, for example, a glycosaminoglycan can be connected to a p(HA-EA) as a graft-copolymer. In some embodiments, the glycosaminoglycan is aldehyde-terminated and is connected to the p(HA-EA) at a primary amine. A p(HA-EA) with pendant amino groups on the polymer backbone may be produced by a method that comprises polymerizing a p(HA-EA) with an acid-terminated unit formed by reacting di-p-nitrophenyl sebacate and ε-carbobenzoxy-L-lysine in a suitable solvent such as, for example, DMF or THF. The p(HA-EA) can be combined with the acid-terminated unit using a carbodiimide.

In the coupling of a glycosaminoglycan to a p(HA-EA), a mixed population of sebacic acid and sebacic acid coupled to protected lysines can be blended and reacted with the p(HA-EA) to form diblock copolymers of a predetermined design. The temperature of the reaction ranges from about 25° C. to about 150° C., from about 50° C. to about 125° C., from about 80° C. to about 100° C., or any range therein. The reaction occurs for a time ranging from about 1 hour to about 24 hours, from about 6 hours to about 18 hours, from about 10 hours to about 14 hours, or any range therein. The carbobenzoxy protecting group can be removed with hydrogenolysis over a palladium-on-carbon catalyst using the method described above. In some embodiments, a glycosaminoglycan such as, for example, an aldehyde-functionalized heparin, can be connected to the p(HA-EA) by

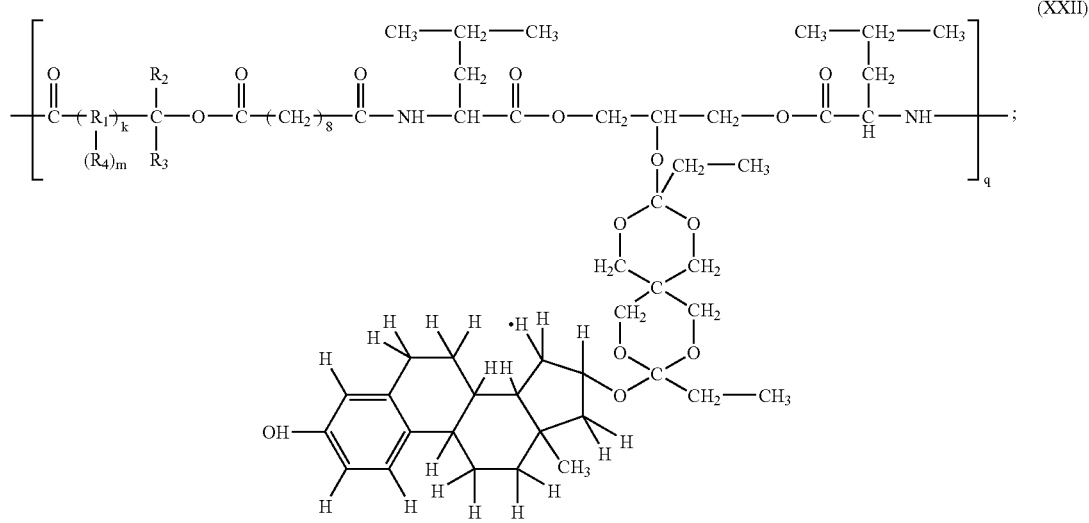

wherein $R_1$ through $R_4$, k, m, and q are defined above.

In formula (XXII), the diacid is sebacic acid, the amino acid is leucine, X is estradiol and $L_2$ is an orthoester known as 3,9-diethylidene-2,4,8,10-tetraoxaspiro-[5,5]-undecane (DETOSU), which is more labile than an ester. To make the polymer of formula (XXII), one equivalent of glycerol can be combined with two equivalents of leucine to obtain an amino-terminated polymeric subunit. Next, a p(HA-EA) can be combined with sebacic acid and the amino-terminated polymeric subunit to obtain a hydroxy-functional p(HA-EA). Estradiol can then be combined with 3,9-diethylidene-2,4,8,10-tetraoxaspiro-[5,5]-undecane (DETOSU) to form an estradiol-DETOSU moiety. The hydroxy-functional reductive amination using sodium cyanoborohydride (NaCNBH$_3$) and a DMF/water solvent. In other embodiments, the glycosaminoglycan can be hyaluronic acid or a derivative thereof.

A PEA can also be connected to a PHA as a graft copolymer in a similar manner. In some embodiments, the PHA can have a backbone that contains all hydroxyalkanoates. In other embodiments, the backbone of the polymer can be a copolymer of PHA and PEA. In other embodiments, the backbone of the polymer can be a copolymer of p(HA-EA) and PEG. In other embodiments, the polymer can be a copolymer of p(HA-EA) and any other polymer taught herein.

In some embodiments, the number average molecular weight of the PEA in a PEA-PHA graft copolymer can range from about 1000 to about 60,000, from about 1000 to about 50,000, from about 1000 to about 40,000, from about 1500 to about 35,000, from about 1500 to about 30,000, from about 1750 to about 25,000, from about 2000 to about 20,000, from about 2,000 to about 15,000, from about 2000 to about 10,000, or any range therein.

II. Agent as a Copolymer

The methods of the present invention can be designed to produce a variety of copolymers such as graft copolymers, an AB copolymer, an ABA copolymer, or an ABABAB . . . multi-block copolymer by activating either one or both ends of the agent polymer and the polyester. The AB-type copolymers result when the two polymers only have a single active end. Copolymers of the ABA-type result where one polymer has one active end and the other polymer has two active ends. Copolymers of the ABABAB . . . -type result where both polymers have two active ends.

A polymeric agent can be connected to a p(HA-EA) as a copolymer and can be any agent taught herein. In some embodiments, the agents include, but are not limited to, poly(alkylene glycols) such as, for example, poly(ethylene glycol) and poly(propylene glycol); phosphorylcholine; poly (N-vinyl pyrrolidone); poly(ethylene oxide); poly(acrylamide methyl propane sulfonic acid); poly(2-hydroxyethyl methacrylate), poly(3-hydroxypropyl methacrylamide), poly(styrene sulfonate); saccharides such as, for example, carboxymethylcellulose; sulfonated polysaccharides such as, for example, sulfonated dextran; sulfated polysaccharides such as, for example, sulfated dextran and dermatan sulfate; and any derivatives, analogs, homologues, congeners, salts, copolymers and combinations thereof. In other embodiments, the agents can include, but are not limited to, glycosaminoglycans such as, for example, hyaluronic acid, heparin, hirudin, dermatan sulfate, chondroitin sulfate; chitin; chitosan; and any derivatives, analogs, homologues, congeners, salts, copolymers and combinations thereof.

In other embodiments, the agents can be prohealing such as, for example, poly(ester amides), elastin, silk-elastin, collagen; chondroitin sulfate; peptide sequences such as, for example, atrial natriuretic peptide (ANP), and those comprising Arg-Gly-Asp (RGD); and any derivatives, analogs, homologues, congeners, salts, copolymers and combinations thereof. In other embodiments, the agents can be non-thrombotics such as, for example, thrombomodulin; antimicrobials such as, for example, the organosilanes; and any derivatives, analogs, homologues, congeners, salts, copolymers and combinations thereof.

1. p(HA-EA)s Comprising Glycosaminoglycans such as Heparin or Hyaluronic Acid

A graft copolymer of a p(HA-EA) and a glycosaminoglycan such as heparin or hyaluronic acid, or a block copolymer of a p(HA-EA) with an endblock of a glycosaminoglycan such as heparin or hyaluronic acid can be prepared. In some embodiments, these copolymers can be prepared by combining an amino-functionalized p(HA-EA), such as an amino-terminated p(HA-EA), with an aldehyde-functionalized heparin. An example of an aldehyde-functionalized heparin can be represented by formula (XXIII):

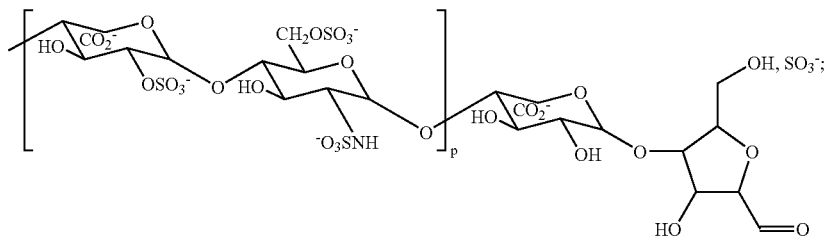

(XXIII)

wherein p is an integer not equal to 0.

The aldehyde-functionalized heparin can be combined, for example, with an amino-functional p(HA-EA) in DMF solvent at 40° C., and dissolved. NaCNBH$_3$ is added to reduce the Schiff base formed and the solution is stirred for 24-48 hours to produce a p(HA-EA)-heparin copolymer structure, either graft or block, depending on the placement of the heparin.

An ABA block-copolymer of PHA and heparin with PHA as the B block, can be prepared by combining a carboxyl-terminated PHA with an aldehyde-functionalized heparin. The carboxyl-terminated PHA is first activated with, for example, EDC or DCC and then combined with a large excess of adipic dihydrazide to prepare an amino-functionalized PHA. The heparin is then coupled to the p(HA-EA) by reductive amination as described above. Alternatively, an aldehyde-functionalized heparin can be treated with ammonia or n-butylamine in the presence of a reducing agent such as, for example, sodium borohydride (NaBH$_4$), potassium borohydride (KBH$_4$), or sodium cyanoborohydride (NaCNBH$_3$), to produce an amino-functionalized heparin. The carboxyl-terminated p(HA-EA) can be activated with, for example, EDC or DCC, and combined with the amino-functionalized heparin.

It should be appreciated that, in some embodiments of the present invention, the agent may be any biobeneficial agent that can enhance the biocompatibility or non-fouling properties of a p(HA-EA) polymer, as well as modify a physical/mechanical property of the polymer. For example, hyaluronic acid can be a polymeric agent used to form a p(HA-EA)-hyaluronic acid copolymer, such as a graft copolymer or an end-block copolymer. Hyaluronic acid has free carboxyl groups, and an aldehyde-derivatized hyaluronic acid can be made, for example, by oxidizing hyaluronic acid with nitrous acid or periodate. The aldehyde-derivatized hyaluronic acid can then be combined with a polyester as described above.

A p(HA-EA) that is multifunctional, such as a p(HA-EA) that is both carboxyl-terminated and hydroxyl-terminated, for example, can be analyzed using standard analytical techniques to determine a ratio of carboxyl groups to hydroxyl groups. The same is true of a p(HA-EA) composition that also contains amino functionality. Knowing the ratio of functionalities will allow one skilled in the art to decide whether to connect the polymeric agent to the hydroxyl ends, the amino ends, or the carboxyl ends of a p(HA-EA) composition. A skilled artisan can protect groups on the p(HA-EA) such as amino groups, for example, with benzyl chloroformate to reduce undesirable side conjugation when combining a carboxyl-terminated p(HA-EA) with an aldehyde derivative that was converted to a hydrazide of a glycosaminoglycan.

p(HA-EA)s Containing Poly(ethylene glycol) Blocks

A block copolymer of p(HA-EA) and PEG can be prepared using a variety of techniques. Some purposes for adding PEO functionality to a p(HA-EA) are discussed above. In one embodiment, a p(HA-EA) with a hydroxyl and a carboxyl endgroup can be combined with a PEG possessing a hydroxyl and a carboxyl endgroup (Nektar Corp.) in the presence of, for example, EDC or DCC to form the following triblock structure represented by formula (XXIV):

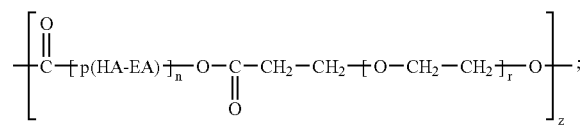

(XXIV)

wherein n, r, and z are integers not equal to 0; and n and z are described above.

In another embodiment, an amino-terminated p(HA-EA) can be combined with a dicarboxyl-terminated PEG (Nektar Corp.) in the presence of, for example, EDC or DCC. In another embodiment, either a succinimidyl derivative of mPEG (Nektar Corp.) or an isocyanate-terminated mPEG (Nektar Corp.) can be reacted with an amino-terminated p(HA-EA) under conditions known to one of skill in the art. In another embodiment, the carboxyl group of a carboxyl-terminated p(HA-EA) can be activated with, for example, EDC or DCC and combined with an amino-terminated mPEG (Nektar Corp.). In another embodiment, an amino-terminated mPEG can be combined with a high molecular weight p(HA-EA) in the presence of a base catalyst through amination of ester groups. In another embodiment, an amino-terminated p(HA-EA) can be combined with ethylene oxide in a living polymerization reaction that forms a PEG block, and which is an unterminated anionic polymerization kept alive and controlled by maintaining a pure system. A living polymerization reaction can be stopped through addition of a terminating agent such as, for example, water.

The p(HA-EA)-PEG copolymer shown above is an AB-block copolymer. In some embodiments, r can range from about 1 to about 2500, from about 10 to about 2000; from about 20 to about 1500, from about 50 to about 1500, from about 100 to about 2300, from about 1000 to about 2300, and any range therein; n and p can independently range from about 1 to about 1500, from about 5 to about 1000; from about 10 to about 500, from about 20 to about 500, from about 30 to about 1300, from about 50 to about 1500, and any range therein.

In another embodiment, an amino-terminated p(HA-EA) can be combined with a carboxyl-terminated PEG (Nektar Corp.) in the presence of, for example, EDC or DCC. In another embodiment, either a succinimidyl derivative of mPEG (Nektar Corp.) or an isocyanate-terminated mPEG (Nektar Corp.) can be reacted with a hydroxyl-, amino-, or sulphydryl-functionalized p(HA-EA) under conditions known to those of skill in the art. In another embodiment, the carboxyl group of a carboxyl-terminated p(HA-EA) can be activated with, for example, EDC or DCC and combined with an amino-terminated PEG (Nektar Corp.) In another embodiment, an amino-terminated PEG can be combined with a high molecular weight p(HA-EA) in the presence of an acid or base catalyst through amination of ester groups in a high molecular weight p(HA-EA). In another embodiment, an amino-terminated p(HA-EA) can be combined with ethylene oxide in a living polymerization reaction, which is an unterminated, anionic polymerization kept alive and controlled by maintaining a pure system. A living polymerization reaction can be killed through addition of a terminating agent such as, for example, water.

Forming a Coating

In some embodiments of the invention, the compositions are in the form of coatings for medical devices such as, for example, a balloon-expandable stent or a self-expanding stent. There are many coating configurations within the scope of the present invention, and each configuration can include any number and combination of layers. In some embodiments, the coatings of the present invention can comprise one or a combination of the following four types of layers: (a) an agent layer, which may comprise a polymer and an agent or, alternatively, a polymer free agent; (b) an optional primer layer, which may improve adhesion of subsequent layers on the implantable substrate or on a previously formed layer; (c) an optional topcoat layer, which may serve as a way of controlling the rate of release of an agent; and (d) an optional biocompatible finishing layer, which may improve the biocompatibility of the coating.

In one embodiment, the agent layer can be applied directly to at least a part of an implantable substrate as a pure agent to serve as a reservoir for at least one bioactive agent. In another embodiment, the agent can be combined with a biodegradable polymer as a matrix, wherein agent may or may not be bonded to the polymer. In another embodiment, the optional primer layer can be applied between the implantable substrate and the agent layer to improve adhesion of the agent layer to the implantable substrate and can optionally comprise an agent. In another embodiment, a pure agent layer can be sandwiched between layers comprising biodegradable polymer. In another embodiment, the optional topcoat layer can be applied over at least a portion of the agent layer to serve as a membrane to control the rate of release of the bioactive agent and can optionally comprise agent. In another embodiment, the biocompatible finishing layer can also be applied to increase the biocompatibility of the coating by, for example, increasing acute hemocompatibility and can also comprise an agent.

The inventive compositions can be used for one or any combination of layers. In some embodiments, any of the other polymers taught herein can be used as one of the layers or can be blended or crosslinked with the p(HA-EA) embodiments. Each layer can be applied to an implantable substrate by any method including, but not limited to, dipping, spraying, pouring, brushing, spin-coating, roller coating, meniscus coating, powder coating, inkjet-type application or a combination thereof. In one example, each of the layers can be formed on a stent by dissolving one or more biodegradable polymers, optionally with a non-biodegradable polymer, in one or more solvents and either (i) spraying the solution on the stent or (ii) dipping the stent in the solution. In this example, a dry coating of biodegradable polymer may be formed on the stent when the solvent evaporates.

The formation of each layer may involve use of a casting solvent. A casting solvent is a liquid medium within which a polymer can be solubilized to form a solution that may be applied as a coating on a substrate. The casting solvent must be selected to avoid adversely affecting an underlying material such as, for example, an underlying primer layer or a bare stent structure. In one example, a material used to form the primer layer is soluble in a highly polar casting solvent but is reasonably insoluble in a low polarity casting solvent. A material is "reasonably insoluble" in a solvent when the material does not solubilize to an extent great enough to significantly affect the performance of the resulting product, meaning that the product can still be used for its intended purpose. In this example, an overlying agent layer that is soluble in a low polarity casting solvent can be applied to the underlying primer layer without disrupting the structure of primer layer.

The casting solvent may be chosen based on several criteria including, for example, its polarity, ability to hydrogen bond, molecular size, volatility; biocompatibility, reactivity and purity. Other physical characteristics of the casting solvent may also be taken into account including the solubility limit of the polymer in the casting solvent, the presence of oxygen and other gases in the casting solvent, the viscosity and vapor pressure of the combined casting solvent and polymer, the ability of the casting solvent to diffuse through an underlying material, and the thermal stability of the casting solvent.

One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Exemplary casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Representative examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures.

A medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30° C. to about 200° C., from about 35° C. to about 190° C., from about 40° C. to about 180° C., from about 45° C. to about 175° C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

The following examples are provided to further illustrate embodiments of the present invention.

EXAMPLE 1

Preparation of carboxyl-terminated, hydroxyl-terminated, and amino-terminated PHAs A hydroxyl-terminated PHA can be prepared by several routes. In one route, a hydroxyl-acid compound such as lactic acid or $\epsilon$-hydroxycaproic acid can be polymerized using acid catalysis, and dehydrating conditions, to produce a low molecular weight PHA with a hydroxyl and a carboxyl endgroup. In the presence of coupling agents such as DCC, an amine-hydroxyl compound such as ethanolamine can be coupled to the carboxyl endgroup resulting in a hydroxyl endgroup. Using the same PHA with a hydroxyl and carboxyl endgroups, the carboxyl endgroup can be selectively reduced to hydroxyl with borane. In another route, ring opening polymerization can be performed using a dihydric initiator, such as a diol, and a cyclic lactone.

1,6-hexanediol (14.77 gm (0.125 mole) can be added to a 250 ml, three-necked flask equipped with magnetic stirring, vacuum, and argon purge. Using an oil bath, the diol can be heated to 60° C. and stirred under vacuum for two hours to remove water. The flask can be purged with argon, D,L-lactide (108.0 g, 0.75 mole) can be added, and the vacuum can be applied with stirring for another 30 minutes. After purging with argon, the flask can be heated to 140° C., and polymerization can be initiated by addition of 10.8 ml of a 5% (w/w) solution of stannous octoate in dry toluene. After stirring for 24 hours, the reaction solution can be cooled and poured into 500 ml of cold methanol to precipitate the polymer. The polymer can be washed with methanol/petroleum ether and dried under vacuum.

A carboxyl-terminated PHA can be prepared by several routes. In one route, a hydroxyl-acid compound such as lactic acid or $\epsilon$-hydroxycaproic acid can be polymerized using acid catalysis and dehydrating conditions to produce a low molecular weight PHA with a hydroxyl and a carboxyl endgroup. This compound can be reacted with succinic anhydride to convert the hydroxyl group to a carboxyl group. Otherwise, a PHA can be made by ring opening polymerization using a diol initiator which has two hydroxyl endgroups.

The poly(D,L-lactide) polymer from above (25 g, 0.0255 mole) and succinic anhydride (5.1 g, 0.051 mole) can be dissolved in 100 ml of anhydrous chloroform. The solution can be stirred at 40° C. overnight. The reaction solution can be cooled and poured into 1000 ml of cold methanol to precipitate the polymer. The polymer can be washed with methanol/petroleum ether and dried under vacuum. 1,3-dicyclohexylcarbodiimide (DCC) (0.103 g, $5 \times 10^{-4}$ mole) and 4-dimethylaminopyridine (0.0012 g, $1 \times 10^{-5}$ mole) can be added. After stirring at room temperature for 24 hours, the reaction solution can be centrifuged to precipitate the dicyclohexylurea formed, and the supernatant solution can be poured into 150 ml of cold methanol to precipitate the polymer. After collection by filtration, the polymer can be washed with methanol/petroleum ether and dried under vacuum.

An amino-terminated PHA can be prepared by several routes. In one route, a hydroxyl functional PHA can be reacted with aziridine. In another route, the hydroxyl functional PHA can be first derivatized with tosyl chloride, tresyl chloride, or trifluoromethanesulfonyl choride. The resulting derivative can then be reacted with an excess of an amine such as ammonia, ethanediamine, 1,4-butanediamne, or 1,5-pentanediamine. In yet another route, the hydroxyl functional PHA can be reacted with an excess of diisocyanate, which can then be hydrolyzed with water to yield the amino-terminated PHA.

The poly(D,L-lactide) polymer from above (25 g, 0.0255 mole), hexamethylene diisocyanate (13.89 g, 0.102 mole), and stannous octoate (0.4 gm, 0.001 mole) can be dissolved in 200 ml of anhydrous chloroform. The solution can be stirred at 40° C. for 2 hours. The reaction solution can be cooled and poured with agitation into 1000 ml of deionized water. After stirring at ambient temperature for 2 hours, the chloroform layer can be isolated and added to 1000 ml of methanol. The precipitated polymer can be washed with methanol/petroleum ether and dried under vacuum. This procedure yields a di-amino-terminated poly(D,L-lactide).

EXAMPLE 2

Preparation of the p(HA-EA) of Formula (XVII)

Three components are needed to prepare this polymer: a PHA with carboxyl and hydroxyl endgroups, a benzyl ester protected lysine, and sebacoyl chloride.

Preparation of poly(caprolactone) with carboxyl and hydroxyl endgroups

ε-hydroxycaproic acid (100 gm, 0.757 mole), p-toluenesulfonic acid monohydrate (14.39 gm, 0.0757 mole), and toluene (350 ml) can be added to a 1000 ml, three necked flask equipped with argon purge, mechanical stirrer, oil bath, and Dean-Stark trap with reflux condenser. The solution can be heated to reflux, and the reaction can be run until 12.26 ml of water is collected in the Dean-Stark trap, indicating a polymer of approximately 1158 Daltons molecular weight. After cooling, the solution can be added to deionized water (500 ml) and stirred for 20 minutes. The toluene layer can be isolated and extracted with 1 N sodium bicarbonate (400 ml), followed by two portions of deionized water (400 ml). After adding the toluene phase to methanol (1000 ml), the polymer can be isolated by filtration and dried for 48 hours under a vacuum of 1 torr at 40° C.

Preparation of poly(caprolactone)-N-L-lysine benzyl ester monotosylate

The poly(caprolactone) polymer from above (50 gm, 0.043 mole), the di-p-toluenesulfonic acid salt of L-lysine benzyl ester (25.07 gm, 0.043 mole), triethylamine (4.35 gm, 0.043 mole), and tetrahydrofuran (THF) (200 ml) can be added to a 500 ml, 3-necked flask equipped with argon purge and mechanical stirrer. After dissolution, DCC (8.87 gm, 0.043 mole) ican be added, and the solution can be stirred overnight at ambient temperature. The solution can be filtered to remove the dicyclohexylurea formed and slowly added to methanol (1000 ml) with stirring to precipitate the polymer. The polymer can be redissolved in chloroform (200 ml), precipitated in isopropyl alcohol (1000 ml), and dried under a vacuum of about 1 torr at about 40° C. for about 48 hours.

Preparation of co-poly[N,O-adipoyl-L-lysine benzyl ester-polycaprolactone]

Poly(caprolactone)-N-L-lysine benzyl ester monotosylate (50 gm, 0.0323 mole), triethylamine (10.79 gm, 0.107 mole), and anhydrous 2-butanone (125 ml) can be added to a 500 ml, 3-necked flask equipped with mechanical stirrer, argon inlet, 50 ml addition funnel, and ice bath. After dissolution, a solution of adipoyl chloride (5.91 gm, 0.0323 mole) in anhydrous 2-butanone (25 ml) can be added with stirring for over 30 minutes while maintaining the reaction at 0° C. The reaction can be allowed to warm to room temperature and stirred for 4 more hours. The solution can be added to a deionized water (1000 ml) with stirring to precipitate the polymer. The polymer can be redissolved in THF (200 ml) and reprecipitated in deionized water (1000 ml) with stirring. The polymer can be redissolved in chloroform (500 ml) and filtered through a dry disc apparatus (Horizon Technologies, Atkinson, N.H.) to remove water. The solution can be concentrated by rotary evaporation, poured into Teflon trays, and dried at about 40° C. under a vacuum of about 1 torr for about 48 hours.

Hydrogenolysis of co-poly[N,O-adipoyl-L-lysine benzyl ester-polycaprolactone]

Palladium powder (5 gm, 0.047 mole) can be added to a 1000 ml flask equipped with an argon inlet, vacuum line, and hydrogen gas inlet, wherein vacuum can be applied for 30 minutes. After purging with argon, THF can be added (500 ml) and hydrogen bubbled through the solution for 30 minutes. Co-poly[N,O-adipoyl-L-lysine benzyl ester-polycaprolactone] (50 gm) can be added under argon, dissolved, and the solution stirred with a steady bubbling of hydrogen through the solution for 12 hours. The palladium can be removed by filtration, and the THF solution can be added dropwise with stirring to deionized water (1500 ml). After isolation by filtration, the polymer can be redissolved in chloroform (500 ml), and filtered through a dry disc apparatus (Horizon Technologies, Atkinson, N.H.) to remove water. The solution can be concentrated by rotary evaporation, poured into Teflon trays, and dried at about 40° C. under a vacuum of about 1 torr for about 48 hours.

Coupling of mPEG-$NH_2$ to co-poly[N,O-adipoyl-L-lysine-polycaprolactone]

Co-poly[N,O-adipoyl-L-lysine-polycaprolactone] (10 gm, 0.00689 mole carboxyl), N-hydroxysuccinimide (0.872 gm, 0.00758 mole), and anhydrous THF (150 ml) can be added to a 250 ml, 3-necked flask equipped with argon purge and magnetic stirrer. After dissolution, dicylohexylcarbodiimide (1.56 gm, 0.00758 mole) can be added as a solution in anhydrous THF (10 ml). The solution can be stirred at ambient temperature for 16 hours, and the precipitated dicyclohexylurea can be removed by vacuum filtration. In a separate 250 ml, 3-necked flask, the solution can be stirred under argon while methoxy-poly(ethylene glycol)-amine MW=559.7 (3.856 gm, 0.00689 mole, Quanta Biodesign, Powell, Ohio) can be added. After stirring at ambient temperature for 18 hours, the solution can be added dropwise to deionized water (600 ml). After isolation by filtration, the polymer can be redissolved in chloroform (100 ml) and filtered through a dry disc apparatus (Horizon Technologies, Atkinson, N.H.) to remove water. The solution can be concentrated by rotary evaporation, poured into Teflon trays, and dried at about 40° under a vacuum of about 1 torr for about 48 hours. This procedure yields a polymer of formula XVII with a pendant mPEG group having a 559 Dalton molecular weight and a weight fraction of mPEG in the polymer of about 28%.

EXAMPLE 3

Preparation of the p(HA-EA) of Formula (XIX)

This preparation begins with the co-poly[N,O-adipoyl-L-lysine-polycaprolactone] possessing a free carboxyl from Example 2. Co-poly[N,O-adipoyl-L-lysine-polycaprolactone] (10 gm, 0.00689 moles carboxyl groups), 4-hydroxyl-2,2,6,6-tetramethylpiperidinyl-1-oxyl (1.19 gm, 0.00689 mole) and anhydrous THF (90 ml) can be added to a 3-necked, 250 ml flask equipped with magnetic stirrer, argon inlet, ice bath, and 25 ml addition funnel. After dissolution, dicyclohexylcarbodiimide (1.56 gm, 0.00758 mole) can be added, and the solution can be stirred under argon at ambient temperature for 24 hours. After filtration to remove the dicyclohexylurea, the polymer can be precipitated by slow addition to isopropylacetate (500 ml). The remaining solvent can be removed by drying at about 40° under a vacuum of about 1 torr for about 48 hours to yield a polymer of formula (XIX).

EXAMPLE 4

Preparation of the p(HA-EA) of Formula (XX)

This preparation begins with the co-poly[N,O-adipoyl-L-lysine-polycaprolactone] possessing a free carboxyl from Example 2. Co-poly[N,O-adipoyl-L-lysine-polycaprolactone] (10 gm, 0.00689 moles carboxyl groups), and anhydrous THF (90 ml) can be added to a 3-necked, 250 ml flask equipped with magnetic stirrer, argon inlet, ice bath, and 25 ml addition funnel. After dissolution, a solution of thionyl chloride (0.82 gm, 0.00689 mole) in anhydrous THF (10 ml) can be added dropwise over 30 minutes while argon is bubbled through the solution. After stirring for 30 more minutes at 0° C., poly(4-vinylpyridine) (2.17 gm Aldrich, Milwaukee, Wis.) can be added, followed by a solution of 4-carboxyl-2,2,6,6-tetramethylpiperidinyl-1-oxyl (1.38 gm, 0.00689 mole) and anhydrous THF (10 ml) that can be added dropwise over thirty minutes. The solution can be allowed to warm to room temperature and stirred for another hour with a constant purge of argon through the solution. The solution can be filtered to remove the acid scavenger, and the polymer can be precipitated by slow addition to anhydrous isopropylacetate (500 ml). The remaining solvent can be removed by drying at about 40° under a vacuum of about 1 torr for about 48 hours to yield a polymer of formula (XX).

EXAMPLE 5

Preparation of the p(HA-EA) of Formula (XXII)

Preparation of this polymer requires synthesis of a bis-[L-leucine]-1,3-propylene diester-2-one block monomer.

Method of Preparing bis-[L-leucine]-1,3-diester-2-propanone

L-leucine(32.80 gm, 0.25 mole), p-toluenesulfonic acid (104.6 gm, 0.55 mole), 1,3-dihydroxy acetone dimer (22.53 gm, 0.125 mole), and 200 ml of benzene are added to a 3-necked, 1 liter flask. The solution can be heated at 80 C for 8 hours, and condensate can be collected in a Dean Stark trap. The solids are separated from the solvents by roto-evaporation, rinsed in Buchner funnel with water (2, 1 liter portions) and dried in a vacuum oven.

Preparation of poly(caprolactone)-N-bis-[L-leucine]-1,3-diester-2-propanone-monotosylate The poly(caprolactone) polymer from Example 3 (50 gm, 0.043 mole), the di-p-toluenesulfonic acid salt of bis-[L-leucine]-1,3-diester-2-propanone (28.38 gm, 0.043 mole), triethylamine (4.35 gm gm, 0.043 mole), and tetrahydrofuran (THF) (200 ml) can be added to a 500 ml, 3-necked flask equipped with argon purge and mechanical stirrer. After dissolution, DCC (8.87 gm, 0.043 mole) can be added and the solution stirred overnight at ambient temperature. The solution can be filtered to remove the dicyclohexylurea formed and slowly added to methanol (1000 ml) with stirring to precipitate the polymer. The polymer can be redissolved in chloroform (200 ml), precipitated in isopropyl alcohol (1000 ml), and dried under a vacuum of about 1 torr at about 40° C. for about 48 hours.

Preparation of co-poly[N,N-adipoyl-bis-[L-leucine]-1,3-diester-2-propanone-polycaprolactone]

Poly(caprolactone)-N-bis-[L-leucine]-1,3-diester-2-propanone-monotosylate (52.6 gm, 0.0323 mole), triethylamine (10.79 gm, 0.107 mole), and anhydrous 2-butanone (125 ml) can be added to a 500 ml, 3-necked flask equipped with mechanical stirrer, argon inlet, 50 ml addition funnel, and ice bath. After dissolution, a solution of adipoyl chloride (5.91 gm, 0.0323 mole) in anhydrous 2-butanone (25 ml) can be added with stirring over 30 minutes while maintaining the reaction at 0° C. The reaction can be allowed to warm to room temperature and stirred for 4 more hours. The solution can be added to a deionized water (1000 ml) with stirring to precipitate the polymer. The polymer can be redissolved in THF (200 ml) and reprecipitated in deionized water (1000 ml) with stirring. The polymer can be redissolved in chloroform (500 ml) and filtered through a dry disc apparatus (Horizon Technologies, Atkinson, N.H.) to remove water. The solution can be concentrated by rotary evaporation, poured into Teflon trays, and dried at about 40° C. under a vacuum of about 1 torr for about 48 hours.

Method of Preparing Conjugate of estradiol and 3,9-diethylidene-2,4,8,10-tetraoxaspiro-[5,5]-undecane (DETOSU)

Dry THF (40 ml) can be combined with DETOSU (5 gm, 0.0236 mole) and six drops of 1% p-toluenesulfonic acid in THF in a 100 ml flask. A solution of estradiol (6.42 gm. 0.0236 mole) in THF (20 ml) can be slowly added with stirring for over an hour. The estradiol-DETOSU conjugate can be isolated by rotary evaporation.

Method of Preparing the Polymer of Formula (XXII), co-poly[O,N-adipoyl-polycaprolactone-bis-[L-leucine]-1,3-propylenediester-2-DETOSU-Estradiol]

Co-poly[N,N-adipoyl-bis-[L-leucine]-1,3-diester-2-propanone-polycaprolactone] (27.09 gm), dry THF (250 ml), sodium cyanoborohydride (1.05 gm, 0.0167 mole), and p-toluenesulfonic acid (6 drops of a 1% solution) in THF can be added to a 500 ml flask. The mixture can be stirred for two hours at ambient temperature, poured into chloroform (500 ml), and extracted with 3 portions of aqueous sodium bicarbonate (250 ml, 1M portions). Chloroform can be removed by rotary evaporation, and the remaining solvent can be removed by drying overnight in a vacuum oven at ambient temperature. The polymer (22.25 gm), dry THF (250 ml), and the estradiol-DETOSU conjugate (6.64 gm, 0.0137 mole) can be added to a 500 ml flask and stirred at room temperature for two hours. The polymer can be precipitated by slow addition into hexane/ethyl acetate (2 liters, 50/50) with stirring to yield the polymer of formula (XXII).

EXAMPLE 6

Preparation of a p(HA-EA)-glycosaminoglycan Copolymer Using an Aldehyde-Derivatized Glycosaminoglycan Such as the Heparin Shown in Formula (XXIII)

An aldehyde functional heparin obtained by periodate oxidation, or by oxidation with nitrous acid can be obtained from Celsus, Inc., Cincinnati, Ohio. An ABA block copolymer with heparin endblocks can be prepared starting with a di-amino-functional PHA. The di-amino-functional poly(D, L-lactide) from Example 1 (5 gm, 0.00396 mole), 90/10 dimethylformamide/water (250 ml), and aldehyde-heparin (0.0087 aldehyde molar equiv.) can be added to a 500 ml flask equipped with magnetic stirrer and oil bath. After dissolution at 40° C., sodium cyanoborohydride (2.73 gm, 0.044 mole) can be added, and the solution can be stirred at 40° C. for 48 hours. After cooling, the polymer can be precipitated by addition to methanol (1000 ml). After isolation by filtration, the polymer can be dried at about 40° under a vacuum of about 1 torr for about 48 hours.

An AB block heparin-PHA copolymer can be made similarly. Using the hydroxyl and carboxyl functional poly (caprolactone) from Example 2, the carboxyl endgroup can be coupled with adipic dihydrazide using DCC. The resulting hydrazido functional PHA can then be coupled to aldehyde functional heparin via reductive amination.

The poly(caprolactone) from Example 2 (2.5 gm, 0.0021 mole), adipic dihydrazide (0.828 gm, 0.00476 mole), and THF (25 ml) can be added to a 50 ml flask equipped with magnetic stirrer and oil bath. After dissolution, DCC (0.491 gm, 0.00238 mole) can be added, and the solution can be stirred at ambient temperature overnight. After filtration to remove the dicyclohexylurea, the solution can be slowly added to methanol (250 ml) with stirring. The polymer can be isolated by filtration and dried at about 40° under a vacuum of about 1 torr for about 12 hours.

A benzalkonium salt of an aldehyde-functional heparin can be made by dissolving aldehyde-functional heparin in deionized water and adding a stoichiometric amount of benzalkonium chloride per the sodium content of the heparin sodium. The benzalkonium heparin precipitates from solution.

Adipic hydrazide functional poly(caprolactone) (2 gm, 0.00152 mole), THF (100 ml), and aldehyde-heparin (0.00152 aldehyde molar equiv) can be added to a 250 ml flask equipped with a magnetic stirrer and oil bath. After dissolution at 40° C., sodium cyanoborohydride (0.472 gm, 0.0076 mole) can be added, and the solution can be stirred at 40° C. for 48 hours. After cooling, the polymer can be precipitated by addition to deionized water (1000 ml). After isolation by filtration, the polymer can be dried at about 40° under a vacuum of about 1 torr for about 48 hours.

EXAMPLE 7

Preparation of a p(HA-EA) of the Type of Formula (XV)

This preparation uses the di-amino-terminated poly(D,L-lactide) from Example 1, a L-lysine benzyl ester ditosylate, and di-p-nitrophenyl sebacinate. The amino-terminated poly (D,L-lactide) from Example 1 (25 gm, 0.0198 mole), the di-p-toluenesulfonic acid salt of L-lysine benzyl ester (5.69 gm, 0.0098 mole), di-p-nitrophenyl sebacinate (13.2 gm, 0.0296 mole), dry triethylamine (3.0 ml, 0.0216 mole), and anhydrous dimethylformamide (50 ml) can be added to a 3-necked, 500 ml flask equipped with mechanical stirrer, argon inlet and oil bath. The mixture can be stirred and heated at 80 C for 12 hours. The mixture can then be cooled to room temperature, diluted with additional dimethyformamide (250 ml), and added dropwise with stirring to 1% aqueous sodium carbonate (1750 ml). The polymer can be isolated by filtration, redissolved in THF (250 ml) and precipitated by addition to deionized water (1750 ml). After isolation by filtration, the polymer can be dried at about 40° under a vacuum of about 1 torr for about 48 hours to yield a polymer of formula (XV) with a benzyl ester protected lysine. Subsequent hydrogenolysis of the benzyl ester will liberate the lysine carboxyl and allow conjugation of biobeneficial moieties.

EXAMPLE 8

Method of Preparing a p(HA-EA)-PEG Conjugate with an Amino-Terminated p(HA-EA)

An amino-terminated p(HA-EA) can be coupled to PEG by aldehyde coupling/imine reduction, carbodiimide coupling of a carboxyl-terminated PEG, and maleimide coupling of a PEG-maleimide to an amino-terminated p(HA-EA).

A p(HA-EA) (50 g) can be dissolved in anhydrous DMAC (230 g) in the coupling of PEG to amino-terminated p(HA-EA). A PEG-butyraldehyde (MW 1000-50,000, 7.5 g) is combined with sodium cyanoborohydride (1.0 g) and stirred overnight at room temperature under nitrogen. The polymer is precipitated by addition of the solution with stirring in methanol, redissolved in DMAC, reprecipitated in water, and dried under vacuum.

An amino-terminated p(HA-EA) can be conjugated to PEG by carbodiimide coupling of a carboxyl-terminated PEG using DCC/NHS coupling. An amino-terminated p(HA-EA) (50 g) is added to anhydrous THF (116 g; 1-35% w/w). Anhydrous THF (116 g) and carboxyl-terminated PEG (10 kD, 7.0 g, 0.7 mmol), dicyclohexylcarbodiimide (0.15 g; 7.1 mmol) (DCC) is added to a reactor containing N-hydroxysuccinimide (0.10 g/8 mmol) (NHS) to form a mixture. The mixture is stirred under nitrogen for 2 hours at room temperature, and the amino-terminated p(HA-EA) solution is added to the mixture in a dropwise manner, stirred overnight at room temperature, and added dropwise to methanol to form a p(HA-EA)-PEG precipitate. The precipitate is filtered and dried under vacuum.

EXAMPLE 9

A medical article with two layers of coating can be fabricated to comprise everolimus by preparing a first composition and a second composition, wherein the first composition can be an agent layer comprising a matrix of a p(HA-EA) and agent, and the second composition can be a p(HA-EA) topcoat layer. The first composition can be prepared by mixing a functionalized p(HA-EA) with the everolimus in absolute ethanol, sprayed onto a surface of a bare 12 mm Vision™ stent (Guidant Corp.) ("example stent") and dried to form a coating. An example coating technique comprises spray-coating with a 0.014, fan nozzle, a feed pressure of about 0.2 atm and an atomization pressure of about 1.3 atm; applying about 20 µg of wet coating per pass; drying the coating at about 50° C. for about 10 seconds between passes and baking the coating at about 50° C. for about 1 hour after the final pass to form a dry agent layer. A second composition can be prepared by mixing the p(HA-EA) in absolute ethanol and applying the p(HA-EA) using the example coating technique.

EXAMPLE 10

A medical article with three layers of coating can be fabricated to comprise everolimus by preparing a first composition, a second composition and a third composition. The first composition can be a primer layer of a p(HA-EA). The second composition can be a pure agent layer, and the third composition can be a topcoat layer of a p(HA-EA). The first composition can be prepared by mixing about 2% (w/w) of the p(HA-EA) in absolute ethanol and can be applied onto the surface of the example stent using the example coating technique to form a dry primer layer. The dry primer layer can contain about 100 µg of the p(HA-EA). The second composition can be prepared by mixing about 2% (w/w) everolimus in absolute ethanol and applying the mixture to the primer layer using a coating technique to form a pure agent layer comprising everolimus. The third composition can be prepared by mixing about 2% (w/w) of the p(HA-EA) in absolute ethanol and applying the mixture using a coating technique to form a topcoat layer comprising the p(HA-EA).

While particular embodiments of the present invention have been shown and described, those skilled in the art will note that variations and modifications can be made to the present invention without departing from the spirit and scope of the teachings. A multitude of chemical structures, polymers, agents and methods have been taught herein. One of skill in the art is to appreciate that such teachings are provided by way of example only and are not intended to limit the scope of the invention. For example, the chemical structures taught herein are meant to cover all stereoisomerism possible for each chemical structure represented rather than to depict any particular stereoisomerism, unless otherwise specified.

What is claim is:

1. A a poly(hydroxyalkanoate-co-ester amide) polymer of a formula:

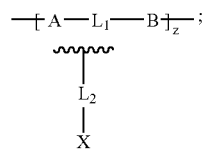

wherein A comprises units derived from a hydroxyalkanoate monomer

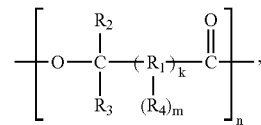

and A:B is less than, greater than, or equal to one;

each $R_1$ comprises a component that is independently selected from a group consisting of alkylenes, alkanoates, alkyl alkanoates, diesters, acylals, diacids, saturated fatty acids, glycerides, and combinations thereof, wherein $R_1$ is selected such that the length of the hydroxyalkanoate monomer does not exceed a length of about 200 nm;

each of $R_2$ and $R_4$ comprise a component that is independently selected from a group consisting of hydrogen; oxygen-containing groups comprising a hydroxyl, carboxyl, carbonyl, alkoxyl, or epoxyl; nitrogen-containing groups comprising an amino, amido, nitro, cyano, isocyanate, azido, diazo, hydrazine, azo, or azoxyl; sulfur-containing groups comprising a thio, thiol, or sulfide; substituted, unsubstituted, hetero-, straight-chained, branched, cyclic, saturated and unsaturated aliphatic radicals; and substituted, unsubstituted, and hetero- aromatic radicals, wherein each of the aliphatic or aromatic radicals of $R_2$ and $R_4$ has from 1 to 10 carbon atoms;

each of $R_3$ comprises a component that is independently selected from a group consisting of oxygen-containing groups comprising a hydroxyl, carboxyl, carbonyl, alkoxyl, or epoxyl; nitrogen-containing groups comprising an amino, amido, nitro, cyano, isocyanate, azido, diazo, hydrazine, azo, or azoxyl; sulfur-containing groups comprising a thio, thiol, or sulfide; substituted, unsubstituted, hetero-, straight-chained, branched, cyclic, saturated and unsaturated aliphatic radicals; and substituted, unsubstituted, and hetero- aromatic radicals, wherein each of the aliphatic or aromatic radicals of $R_3$ has from 1 to 10 carbon atoms;

at least one of $L_1$, B, $L_2$ or X is optional; and at least one of $L_1$, B, $L_2$ or X comprises an oligomer of an ester amide or a poly(ester amide);

wherein, $L_1$ is a linkage connecting A to B, X is an optional moiety, $L_2$ is a linkage connecting X to the polymer, k and m are integers, and n and z are integers not equal to zero.

2. The polymer of claim 1, wherein A comprises units derived from a hydroxyalkanoate selected from the group consisting of 3-hydroxybutyrate, 4-hydroxybutyrate, 3-hydroxyvalerate, 3-hydroxybutyrate-co-valerate, caprolactone, lactide, glycolide, lactide-co-glycolide, and combinations thereof.

3. The polymer of claim 1, wherein at least one of $L_1$, B, $L_2$ or X comprises a therapeutic agent.

4. The polymer of claim 3, wherein the agent is connected to the polymer.

5. The polymer of claim 3, wherein the agent is blended with the polymer.

6. The polymer of claim 1, wherein the poly(ester amide) comprises a component selected from a group consisting of

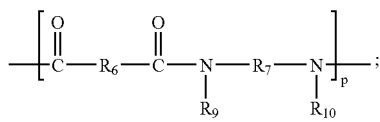

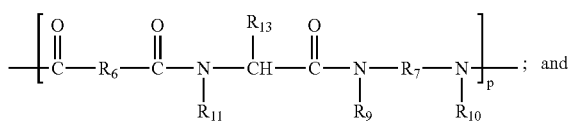

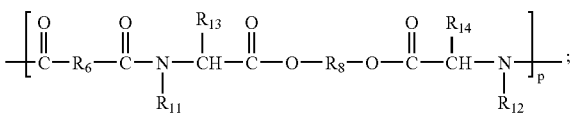

where $R_6$ is optional and comprises a component that is independently selected from a group consisting of substituted, unsubstituted, hetero-, straight-chained, branched, cyclic, saturated and unsaturated aliphatic radicals; and substituted, unsubstituted, and hetero-aromatic radicals;

$R_7$ and $R_8$ comprise a component that is independently selected from a group consisting of substituted, unsubstituted, hetero-, straight-chained, branched, cyclic, saturated and unsaturated aliphatic radicals; and substituted, unsubstituted, and hetero- aromatic radicals;

$R_9$ through $R_{14}$ comprise a component that is independently selected from a group consisting of hydrogen; substituted, unsubstituted, hetero-, straight-chained, branched, cyclic, saturated and unsaturated aliphatic radicals; and substituted, unsubstituted, and hetero-aromatic, radicals; and p is an integer not equal to zero.

7. The polymer of claim 6, comprising

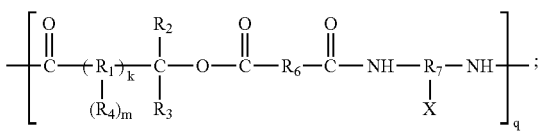

wherein, X is optional and comprises an agent, and q is an integer not equal to zero.

8. The polymer of claim 6, comprising

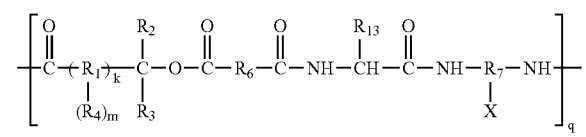

wherein, X is optional and comprises an agent, and q is an integer not equal to zero.

9. The polymer of claim 1, comprising

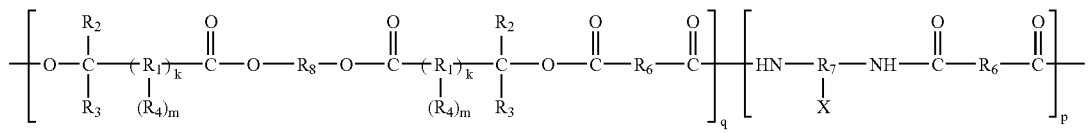

wherein, X is optional and comprises an agent, and q and p are integers not equal to zero;

each $R_6$ is optional and comprises a component that is independently selected from a group consisting of substituted, unsubstituted, hetero-, straight-chained, branched, cyclic, saturated and unsaturated aliphatic radicals; and substituted, unsubstituted, and hetero-aromatic radicals; and, each $R_7$ and $R_8$ comprise a component that is independently selected from a group consisting of substituted, unsubstituted, hetero-, straight-chained, branched, cyclic, saturated and unsaturated aliphatic radicals; and substituted, unsubstituted, and hetero-aromatic radicals.

10. The polymer of claim 1, comprising

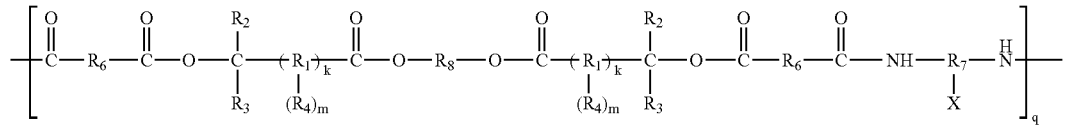

wherein, X is optional and comprises an agent, and q is an integer not equal to zero;
  each $R_6$ is optional and comprises a component that is independently selected from a group consisting of substituted, unsubstituted, hetero-, straight-chained, branched, cyclic, saturated and unsaturated aliphatic radicals; and substituted, unsubstituted, and hetero-aromatic radicals; and,
  each $R_7$ and $R_8$ comprise a component that is independently selected from a group consisting of substituted, unsubstituted, hetero-, straight-chained, branched, cyclic, saturated and unsaturated aliphatic radicals; and substituted, unsubstituted, and hetero-aromatic radicals.

11. The polymer of claim 1, comprising

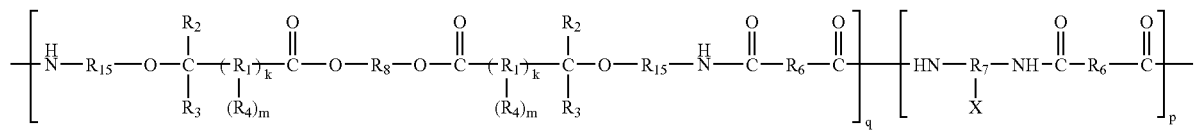

wherein, X is optional and comprises an agent, and q and p are integers not equal to zero;
  each $R_6$ is optional and comprises a component that is independently selected from a group consisting of substituted, unsubstituted, hetero-, straight-chained, branched, cyclic, saturated and unsaturated aliphatic radicals; and substituted, unsubstituted, and hetero-aromatic radicals;
  each $R_7$ and $R_8$ comprise a component that is independently selected from a group consisting of substituted, unsubstituted, hetero-, straight-chained, branched, cyclic, saturated and unsaturated aliphatic radicals; and substituted, unsubstituted, and hetero-aromatic radicals; and,
  each $R_{15}$ comprises a component independently selected from an alkylene, an amide, an acyl or a combination thereof.

12. The polymer of claim 1, wherein at least one of $L_1$, B, $L_2$ or X comprises an agent selected from a group consisting of elastin, silk-elastin, collagen, atrial natriuretic peptide (ANP), Arg-Gly-Asp (RGD); and any derivatives, analogs, homologues, congeners, salts, copolymers and combinations thereof.

13. The polymer of claim 3, wherein the agent comprises a free radical scavenger, a nitric oxide donor, rapamycin, methyl rapamycin, 42-Epi-(tetrazoylyl) rapamycin, everolimus, tacrolimus, paclitaxel, docetaxel, estradiol, clobetasol, idoxifen, tazarotene and any prodrugs, metabolites, analogs, homologues, congeners, or derivatives, salts or combinations thereof.

14. The polymer of claim 13, wherein the free radical scavenger comprises a component selected from a group consisting of 2,2',6,6'-tetramethyl-1-piperinyloxy, free radical; 4-amino-2,2',6,6'-tetramethyl-1-piperinyloxy, free radical; 4-hydroxy-2,2',6,6'-tetramethyl-piperidene-1-oxy, free radical; 4-carboxy-2,2', 6,6'-tetramethyl-1-piperinyloxy, free radical; 2,2',3,4,5,5'-hexamethyl-3-imidazolinium-1-yloxy methyl sulfate, free radical; 16-doxyl-stearic acid, free radical; superoxide dismutase mimic; and analogs, homologues, congeners, derivatives, salts and combinations thereof.

15. The polymer of claim 13, wherein the free radical scavenger comprises a component selected from a group consisting of TEMPO and any analogs, homologues, congeners, derivatives, salts or combinations thereof.

16. The polymer of claim 13, wherein the nitric oxide donor comprises a component selected from the group consisting of S-nitrosothiols, nitrites, N-oxo-N-nitrosamines, substrates of nitric oxide synthase, diazenium diolates and any analogs, homologues, congeners, derivatives, salts and combinations thereof.

17. The polymer of claim 1, wherein $L_1$ or $L_2$ comprises a component selected from a group consisting of ethers, amides, esters, anhydrides, orthoesters, all-aromatic carbonates, acetals, ketals, urethanes, ureas, glycosides, disulfides, siloxanes, and combinations thereof.

18. A medical article comprising the polymer of claim 1.

19. The medical article of claim 18 which is a stent.

20. A method of treating a disorder in a patient comprising implanting in the patient the medical device of claim 19, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

* * * * *